US 6,706,008 B2
United States Patent
Vishnoi et al.

(10) Patent No.: US 6,706,008 B2
(45) Date of Patent: Mar. 16, 2004

(54) AUTOMATED SYSTEM AND METHOD FOR WITHDRAWING COMPOUNDS FROM BLOOD

(75) Inventors: Rohit Vishnoi, Deerfield, IL (US); Richard I. Brown, Northbrook, IL (US); Kyungyoon Min, Gurnee, IL (US); Tom Westberg, Gurnee, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/800,133

(22) Filed: Mar. 6, 2001

(65) Prior Publication Data

US 2002/0128581 A1 Sep. 12, 2002

(51) Int. Cl.[7] ............................................. A61M 37/00
(52) U.S. Cl. ................... 604/5.01; 604/4.01; 604/6.01; 604/6.05; 604/6.11; 604/5.01; 604/6.04
(58) Field of Search .............................. 604/5.01, 4.01, 604/6.01, 6.02, 6.04, 6.11, 6.05; 210/85

(56) References Cited

U.S. PATENT DOCUMENTS

| | | | |
|---|---|---|---|
| 4,096,136 A | 6/1978 | Ayers et al. | |
| 4,420,395 A | 12/1983 | Tanihara et al. | |
| 4,427,777 A | 1/1984 | Goldstein | |
| 4,464,172 A | 8/1984 | Lichtenstein | |
| 4,472,303 A | 9/1984 | Tanihara et al. | |
| 4,479,762 A | 10/1984 | Bilstad et al. | |
| 4,481,827 A | 11/1984 | Bilstad et al. | |
| 4,576,928 A | 3/1986 | Tani et al. | |
| 4,603,010 A | 7/1986 | Ayers et al. | |
| 4,623,628 A | 11/1986 | Maaskant et al. | |
| 4,637,994 A | 1/1987 | Tani et al. | |
| 4,647,280 A | 3/1987 | Maaskant et al. | |
| 4,648,974 A | 3/1987 | Rosskopf et al. | |
| 4,683,889 A | 8/1987 | Edelson | |
| 4,684,521 A | 8/1987 | Edelson | |
| 4,775,482 A | 10/1988 | Thurman | |

(List continued on next page.)

FOREIGN PATENT DOCUMENTS

| | | |
|---|---|---|
| EP | 0 180720 B1 | 6/1990 |
| EP | 0 321 597 B1 | 11/1992 |
| EP | 0 225 867 B1 | 12/1993 |
| EP | 0 420 766 B1 | 3/1995 |
| EP | 0 796 865 A2 | 9/1997 |
| EP | 0 464 872 B1 | 8/2000 |

(List continued on next page.)

OTHER PUBLICATIONS

P. Schuff–Werner, et al., "The HELP–LDL–apheresis multicentre study, an angiographically assessed trial on the role of LDL–apheresis in the secondary prevention of coronary heart disease. II. Final evaluation of the effect of regular treatment on LDL–cholesterol plasma concentrations and the course of cornary heart disease," European Journal of Clinical Investigation (1994) vol. 24, pp. 724–732.

T. Bosch, et al., "Efficacy of lipid apheresis: definitions and influencing factors," The International Journal of Artificial Organs (1995), vol. 18, No. 4, pp. 210–215.

Thomas Bosch, "State of the Art of Lipid Apheresis," Artificial Organs (1996), vol. 20(4), pp. 292–295.

(List continued on next page.)

Primary Examiner—Ira S. Lazarus
Assistant Examiner—Tu Cam Nguyen
(74) Attorney, Agent, or Firm—Andrew G. Kolomayets; Bradford R L Price; Amy L H Rockwell

(57) ABSTRACT

Automated systems and methods for withdrawing a selected compound from blood are disclosed. The systems and methods utilize a disposable fluid circuit mounted on a re-usable hardware component or module. The system withdraws blood from a donor or patient, separates the blood into two or more components and further combines the separated component with a solvent so as to remove a compound from the blood component.

21 Claims, 15 Drawing Sheets

U.S. PATENT DOCUMENTS

| | | | |
|---|---|---|---|
| 4,775,483 A | 10/1988 | Mookerjea et al. | |
| 4,781,838 A | 11/1988 | Crassous et al. | |
| 4,816,162 A | 3/1989 | Rosskopf et al. | |
| 4,842,576 A | 6/1989 | Lysaght et al. | |
| 4,895,558 A | 1/1990 | Cham | |
| 4,908,354 A | 3/1990 | Seidel et al. | |
| 4,923,439 A | 5/1990 | Seidel et al. | |
| 4,935,204 A | 6/1990 | Seidel et al. | |
| 5,133,703 A | 7/1992 | Boehringer et al. | |
| 5,152,743 A | 10/1992 | Gorsuch et al. | |
| 5,194,145 A | 3/1993 | Schoendorfer | |
| 5,203,778 A | 4/1993 | Boehringer et al. | |
| 5,258,149 A | 11/1993 | Parham et al. | |
| 5,298,016 A * | 3/1994 | Gordon | 604/4 |
| 5,354,262 A | 10/1994 | Boehringer et al. | |
| 5,391,143 A | 2/1995 | Kensey | |
| 5,403,917 A | 4/1995 | Boos et al. | |
| 5,437,624 A | 8/1995 | Langley | |
| 5,464,634 A | 11/1995 | Kossovsky et al. | |
| 5,496,637 A | 3/1996 | Parham et al. | |
| 5,514,281 A | 5/1996 | Boos et al. | |
| 5,581,687 A | 12/1996 | Lyle et al. | |
| 5,641,622 A | 6/1997 | Lake et al. | |
| 5,671,135 A | 9/1997 | Jorgensen et al. | |
| 5,679,260 A | 10/1997 | Boos et al. | |
| 5,679,775 A | 10/1997 | Boos et al. | |
| 5,693,232 A | 12/1997 | Brown et al. | |
| 5,733,254 A | 3/1998 | Jones et al. | |
| 5,744,038 A | 4/1998 | Cham | |
| 5,746,708 A * | 5/1998 | Giesler et al. | 604/4 |
| 5,753,227 A | 5/1998 | Strahilevitz | |
| 5,782,792 A | 7/1998 | Jones et al. | |
| 5,846,426 A | 12/1998 | Boos et al. | |
| 5,858,238 A | 1/1999 | McRea et al. | |
| 5,865,784 A | 2/1999 | Faithfull et al. | |
| 5,865,785 A | 2/1999 | Bischof | |
| 5,868,696 A | 2/1999 | Giesler et al. | |
| 5,879,316 A | 3/1999 | Safar et al. | |
| 5,911,698 A | 6/1999 | Cham | |
| 5,916,743 A | 6/1999 | Lake et al. | |
| 5,958,250 A | 9/1999 | Brown et al. | |
| 5,976,388 A | 11/1999 | Carson | |
| 5,980,760 A | 11/1999 | Min et al. | |
| 6,007,725 A | 12/1999 | Brown | |
| 6,039,946 A | 3/2000 | Strahilevitz | |
| 6,042,783 A | 3/2000 | Nagamatsu et al. | |
| 6,071,423 A * | 6/2000 | Brown et al. | 210/782 |
| 6,099,491 A | 8/2000 | Headley et al. | |
| 6,103,126 A | 8/2000 | Boos et al. | |
| 6,106,727 A * | 8/2000 | Krasnoff et al. | 210/739 |
| 6,129,656 A | 10/2000 | Blakeslee et al. | |
| 6,175,420 B1 | 1/2001 | Barry et al. | |
| 6,196,987 B1 | 3/2001 | Holmes et al. | |
| 6,254,567 B1 | 7/2001 | Treu et al. | |
| 6,261,065 B1 | 7/2001 | Nayak et al. | |
| 6,264,890 B1 * | 7/2001 | Boehringer et al. | 422/44 |
| 6,270,673 B1 | 8/2001 | Belt et al. | |
| 6,284,142 B1 * | 9/2001 | Muller | 210/745 |
| 6,284,452 B1 | 9/2001 | Segall et al. | |
| 6,294,094 B1 | 9/2001 | Muller et al. | |
| 6,296,450 B1 | 10/2001 | Westberg et al. | |
| 6,299,784 B1 | 10/2001 | Biesel | |
| 6,306,346 B1 * | 10/2001 | Lindsay | 422/45 |
| 6,315,707 B1 | 11/2001 | Smith et al. | |
| 6,322,488 B1 | 11/2001 | Westberg et al. | |
| 6,325,775 B1 * | 12/2001 | Thom et al. | 604/6.02 |
| RE37,584 E * | 3/2002 | Cham | 210/634 |
| 6,419,822 B2 | 7/2002 | Muller et al. | |
| 2002/0090319 A1 * | 7/2002 | Vandlik et al. | 422/44 |

FOREIGN PATENT DOCUMENTS

| | | |
|---|---|---|
| JP | 01229878 A | 9/1993 |
| JP | 01315338 A | 9/1993 |
| JP | 02060660 A | 9/1993 |
| JP | 5802819 A | 9/1993 |
| JP | 58027559 A | 9/1993 |
| JP | 60246765 A | 9/1993 |
| JP | 63232845 A | 9/1993 |
| JP | 03289966 A | 10/1993 |
| JP | 05057015 A | 11/1993 |
| JP | 06233815 A | 11/1994 |
| JP | 06233816 A | 11/1994 |
| JP | 06237995 A | 11/1994 |
| JP | 06237996 A | 11/1994 |
| JP | 10182694 A | 11/1998 |
| JP | 11060595 A | 5/1999 |
| JP | 11332981 A | 2/2000 |
| WO | WO 89/12390 A1 | 12/1989 |
| WO | WO 91/01808 A1 | 2/1991 |
| WO | WO 95/31727 A1 | 11/1995 |
| WO | WO 95/35155 A1 | 12/1995 |
| WO | WO 97/27889 A1 | 8/1997 |
| WO | WO 98/09659 A1 | 3/1998 |
| WO | WO 98/30620 A1 | 7/1998 |
| WO | WO 99/02565 A3 | 1/1999 |
| WO | WO 01/17584 A1 | 3/2001 |

OTHER PUBLICATIONS

Thomas Bosch, "Lipid Apheresis: From a Heroic Treatment to Routine Clinical Practice," Artificial Organs (1996), vol. 20(5), pp. 414–419.

Eleftherios C. Vamvakas, M.D., PhD., et al., "Selective Extraction of Plasma Constituents," Apheresis: Principles and Practice (1997), pp. 375–407.

T. Bosch, et al., "Low Density Lipoprotein Hemoperfusion by Direct Adsorption of Lipoproteins from Whole Blood (DALI Apheresis): Clinical Experience from a Single Center" (1999), vol. 3(3), pp. 209–213.

Patrick M. Moriarty, M.D., et al., "Low–Density Lipoprotein Apheresis in the Treatment of Atherosclerosis and Other Potential Uses," Current Atherosclerosis Reports (2001), vol. 3, pp. 156–162.

U.S. patent application Ser. No. 09/800,129, Min et al., filed Mar. 2001.

U.S. patent application Ser. No. 09/800,024, Farrell et al.

U.S. patent application Ser. No. 09/800,206, Brown et al.

M. Ferrari, et al., "A New Technique For Hemodilution, Preparation Of Autologous Platelet–Rich Plasma and Intraoperative Blood Salvage In Cardiac Surgery," The International Journal of Artificial Organs, (1987) pp. 47–50, vol. 10, No. 1.

Oliver Habler, et al., "IV Perflubron Emulsion Versus Autologous Transfusion In Severe Normovolemic Anemia: Effects on Left Ventricular Perfusion and Function," The American Physiological Society (1998), pp. 301–318, vol. 197, by Springer–Verlag 1998.

Jorg Hutter, et al., "Effect Of Acute Normovolemic Hemodilution On Distribution Of Blood Flow And Tissue Oxygenation In Dog Skeletal Muscle," The American Physiological Society (1999), pp. 860–866.

Donat R. Spahn, et al., "Perflubron Emulsion Delays Blood Transfusions in Orthopedic Surgery," American Society of Anesthesiologists (1999), pp. 1195–1208.

* cited by examiner

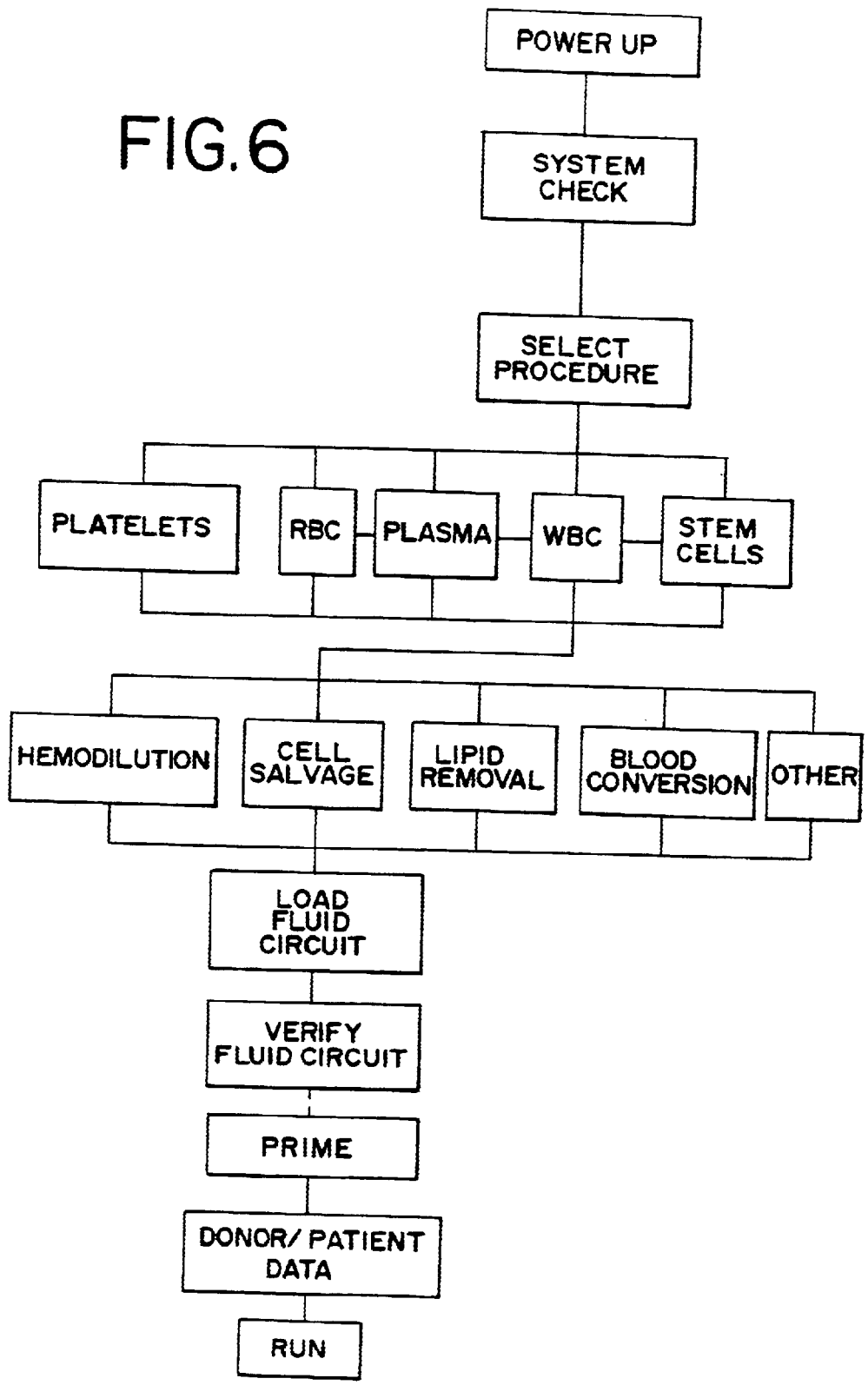

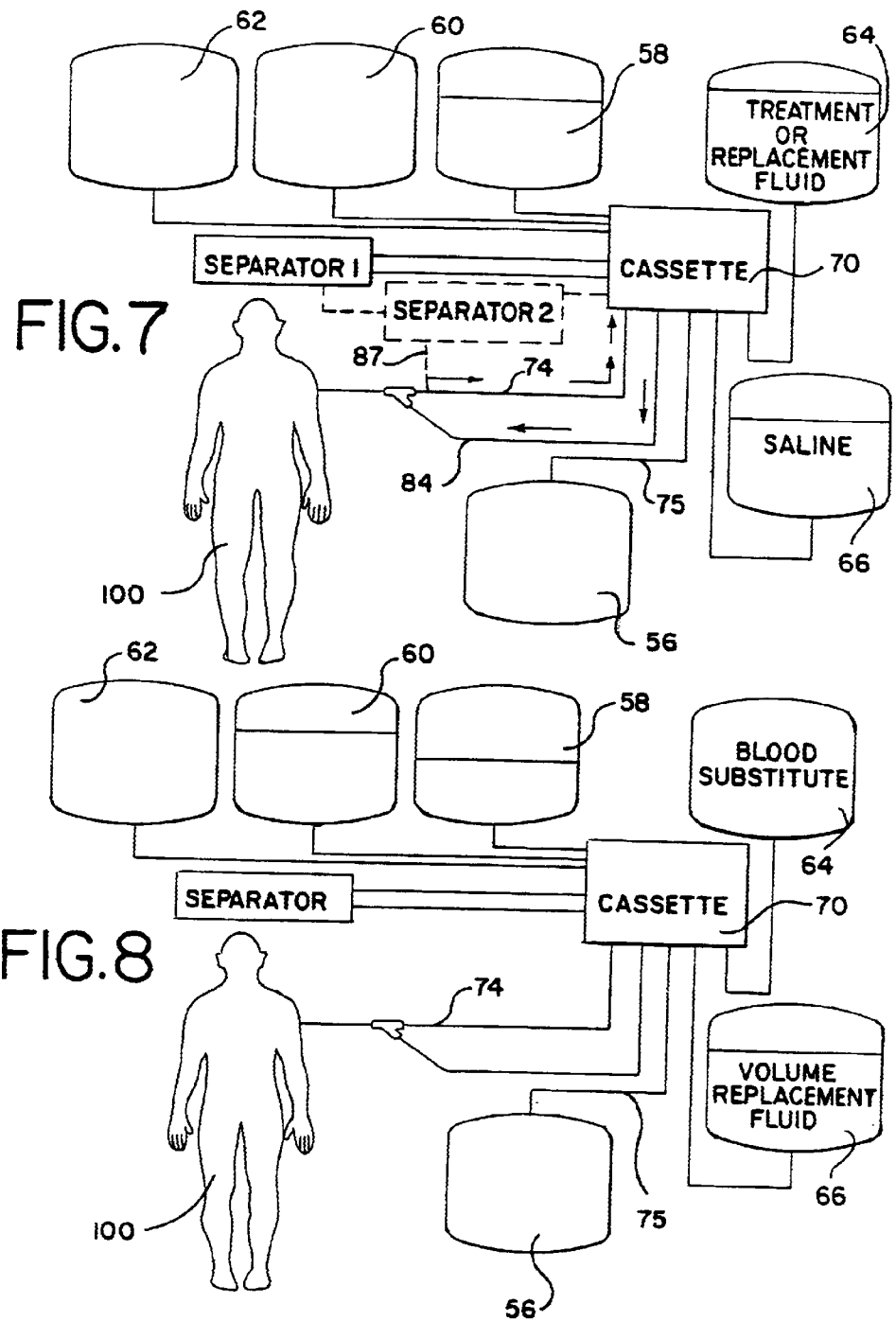

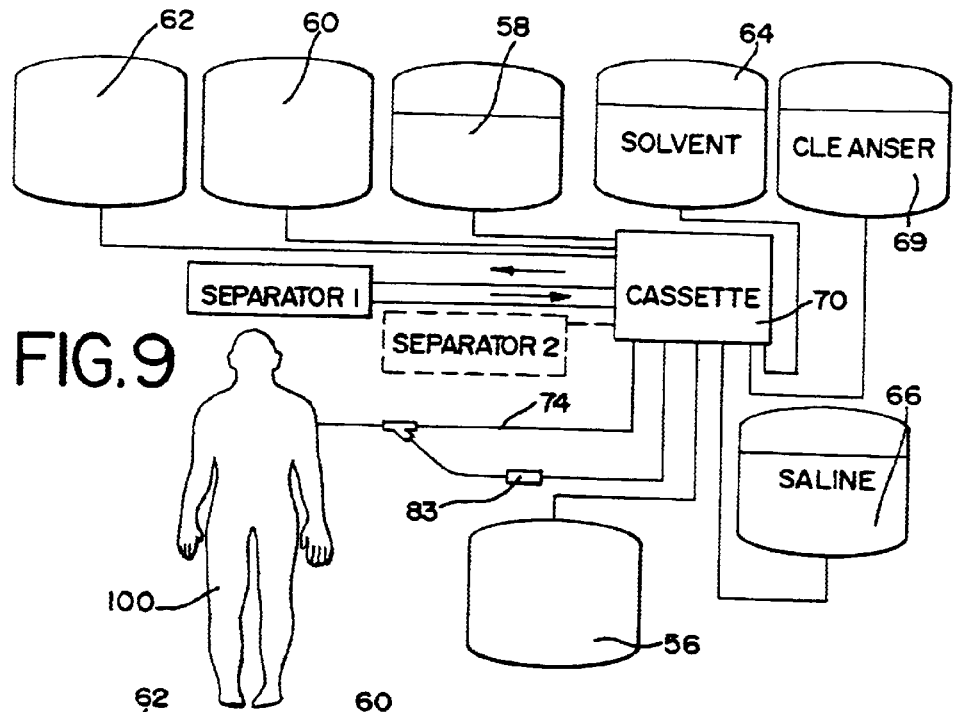
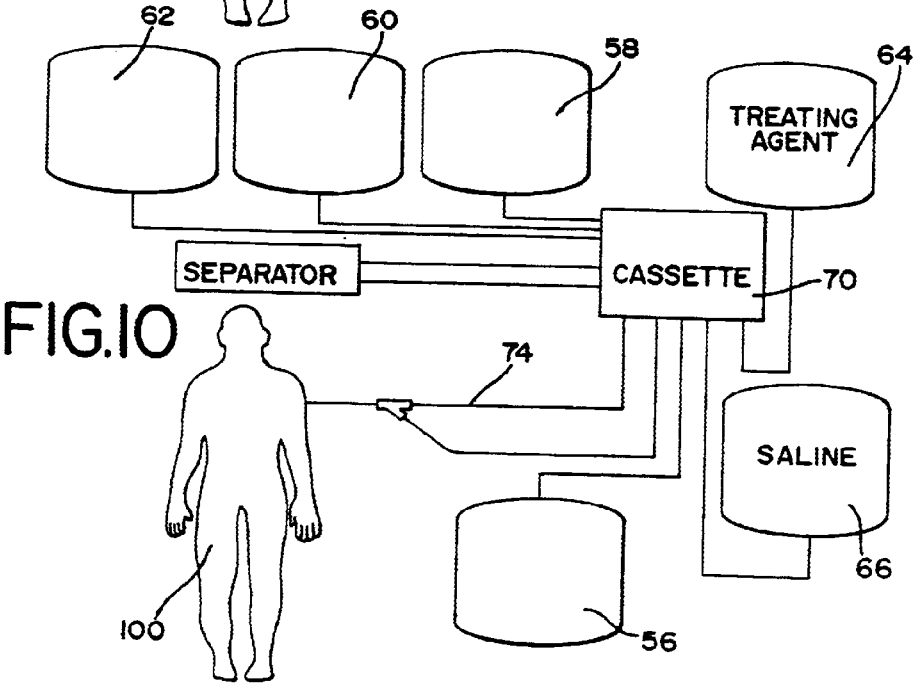

AUTOMATED SYSTEM AND METHOD FOR WITHDRAWING COMPOUNDS FROM BLOOD

The present invention relates, in general, to a highly versatile, automated system for processing blood, blood components, and other fluids included in such processing. More particularly, the present invention relates to an automated system that can separate blood into two or more blood components ("apheresis"), and then perform a further procedure involving one or more of the separated components.

The term "apheresis" means removing whole blood from a patient or donor and separating the blood into two or more components. A separated component can be collected from a healthy donor, and later transfused to a patient in need of the component. Apheresis is also used in therapeutic applications to treat illness by removing diseased or otherwise undesirable components from a patient.

In a basic apheresis procedure, blood is withdrawn from a donor through a needle inserted into the vein of a donor. The needle is attached to one end of a plastic tube which provides a flow path for the blood. The other end of the tube terminates in a container for collecting the blood. The collected blood is then separated in a separator, such as a centrifuge, into its components. The desired blood component which, depending on the procedure, can be red blood cells, platelets, plasma, white blood cells or stem cells may be collected and stored for later transfusion to a patient in need of the blood component.

More recently, "automated" apheresis systems have come into widespread use. These automated systems utilize disposable, pre-sterilized fluid circuits (i.e., tubing sets) through which the blood flows. The fluid circuits are mounted on re-usable hardware devices or modules that have pumps, valves, sensors and the like. These automated systems further include an internal computer and associated software programs (controller) which control many of the processing functions.

For example, in an automated system, blood flow through the fluid circuit, the operation of valves and pumps, may be monitored and regulated by the system. An automated system can be programmed to initiate, terminate or otherwise control certain functions based on patient or donor data (e.g., height, weight, sex, hematocrit). Likewise, an automated system may monitor certain functions with the aid of sensors which can, for example, sense the amount of the collected or withdrawn component. Optical sensors are used to measure the clarity or content of a fluid, or sense the presence or absence of certain components.

Automated apheresis systems are available from several different manufacturers. Examples of commercially available apheresis systems include the AUTOPHERESIS C® Cell Separator and the ANICUS® Cell Separator, sold by Baxter Healthcare Corporation of Deerfield, Ill. The AUTOPHERESIS C® utilizes a separator that includes a chamber and rotating membrane. Blood is introduced into the chamber and the membrane separates the blood into (at least) plasma and red blood cells, or other plasma-depleted blood.

The AMICUS® Cell Separator utilizes a centrifugal separation principle. In the AMICUS® Separator, whole blood is introduced into a dual-chambered or single-chambered container mounted on a rotatable centrifuge. Whole blood is introduced into the first chamber where red blood cells are separated from platelet-rich plasma (PRP). The PRP flows into a second chamber where it is further separated into platelets and platelet-poor plasma. The disposable fluid circuit of AMICUS® uses preformed cassettes with flow paths defined therein, which is mounted on the AMICUS® device. Flow through the flow path is assisted by peristaltic pumps. A more detailed description of the AMICUS®Separator is provided in U.S. Pat. No. 5,868,696, which is incorporated herein by reference.

Recently, a more, portable automated apheresis system has been developed by Baxter Healthcare Corporation. As described in U.S. Pat. No. 6,325,775 entitled "Self-Contained Transportable Blood Processing Device," which is incorporated herein by reference, the portable apheresis system is also based on the principle of centrifugal separation. It includes a re-usable hardware module and a disposable fluid circuit. The fluid circuit includes a cassette with pre-formed flow paths, valving stations and pumping stations.

Other manufacturers such as Gambro BCT, Haemonetics, Dideco and Fresenius also provide automated apheresis systems based on centrifugal or other separation principles.

While efforts continue to develop and provide more efficient, economical and easy-to-use apheresis systems, concerns about the availability and safety of the blood supply, as well as an increased understanding of the role of certain blood components and blood related diseases, have led to the development of additional blood related procedures. These additional procedures often include treatment of the blood component so as to provide a safer or more viable component. Some of the additional procedures may involve eradication or removal of undesired compounds or other substances from blood. Some of these additional procedures may involve replacement of component with another solution. In any case, these procedures often involve many manual steps, several different pieces of equipment or complex fluid circuits. Thus, there exists a need for an automated system that, in addition to separating blood into its components, can carry out one or more other procedures involving the separated components and/or the treatment thereof.

Thus, it would be desirable to provide an automated system that can perform additional procedures using a single piece of re-usable hardware and an easy-to-load, easy-to-use disposable that eliminates the need for many tubing connections and complex routing of tubing. It would also be desirable to provide a single system that does not require regular operator intervention to perform the selected separation and other treatment or processing steps. It would also be desirable to provide a system where all desired separation and processing steps are performed within a single integrated system, and "off-line" treatment using separate devices is not required. It would also be desirable to provide a system that can perform multiple fluid separation, processing and/or treatment steps through automated control of flow through the fluid circuit.

One application where automated separating and processing of blood may be desirable is in the automated pre-surgical donation of blood and administration of a replacement fluid such as a blood substitute and/or oxygen carrier. A manual version of this process is described in U.S. Pat. No. 5,865,784, incorporated herein by reference.

Another application where automated separating and processing blood may be desirable is in the salvaging of red blood cells during surgery on a patient. In cell salvage, blood from a wound area or from the body cavity (i.e., extravascular or "shed" blood) that would otherwise be lost, is collected, processed (or cleaned), and the cleaned blood is returned to the donor. Examples of systems and apparatus used for cell salvage are described in U.S. Pat. No. 5,976,388, which is incorporated herein by reference.

Another application where separating and processing blood may be desirable is in the removal of unwanted substances from blood or a separated blood component such as plasma. For example, the role of cholesterol and low density lipids (LDL) in cardiovascular disease has been well documented. Methods for lipid removal from the plasma of a patient have been developed and are disclosed in U.S. Pat. Nos. 4,895,558, 5,744,038 and 5,911,698, which are incorporated herein by reference.

Still another application where separating and processing blood may be desirable is in the treatment of blood cells. In a particular application, it may be desirable to treat separated red blood cells with enzymes to, for example, convert Type A, B and AB blood cells to the universally acceptable Type O blood cells. Examples of such methods are described in U.S. Pat. Nos. 6,175,420 and 5,671,135, which are incorporated by reference herein.

As described below, there may be additional applications where it may be desired to separate blood into its components for further treatment and/or processing.

Thus, it would be desirable to provide a single system that, in addition to having the ability of withdrawing whole blood and separating it into two or more components, is programmed for, adaptable for, and capable of carrying out at least two or more applications.

SUMMARY OF THE INVENTION

In one aspect, the present invention is directed to an automated system for withdrawing a selected compound from the blood of a patient. The automated system includes a sterile, preassembled, disposable fluid circuit that includes means for withdrawing blood from a patient. The fluid circuit further includes a separation chamber that includes a first sub-chamber for separating a blood component from blood and a second sub-chamber for separating a combination of the blood component and a solvent into a first phase which substantially includes a compound-depleted blood component and a second phase that substantially includes the solvent and the compound.

The fluid circuit further includes a container containing a solvent where the solvent is adapted for extracting a selected compound from the blood component, and means for combining the solvent with the blood. Solvent removal means and means for returning the compound-depleted blood component to the patient are provided.

The fluid circuit further includes a flow control cassette having preformed flow path segments formed therein and separated by valve stations for controlling communication between the segments.

The automated system also includes a re-usable device that includes a means for receiving the chamber and for separating the blood component from the remainder of the blood. The re-usable module also includes means for cooperating with the valve stations to control the flow of the fluid through the preformed flow paths.

In a further, more particular aspect, the fluid circuit may include a first separation means based on a first separation principle for separating (from blood) a blood component including a compound, and a second separation means based on a second separation principle for separating the combination of the blood component and solvent into first and second phases.

BRIEF DESCRIPTION OF THE DRAWINGS

FIG. 6 is a flow diagram showing the steps performed in the operation of the automated system of the present invention.

FIG. 7 depicts the fluid circuit for a system and procedure embodying the present invention.

FIG. 8 depicts the fluid circuit for an automated hemodilution system and procedure embodying the present invention.

FIG. 9 depicts the fluid circuit for an automated plasma treatment system and procedure embodying the present invention.

FIG. 10 depicts the fluid circuit for an automated cell treatment system and procedure embodying the present invention.

DESCRIPTION OF THE PREFERRED EMBODIMENTS

Figure 1:
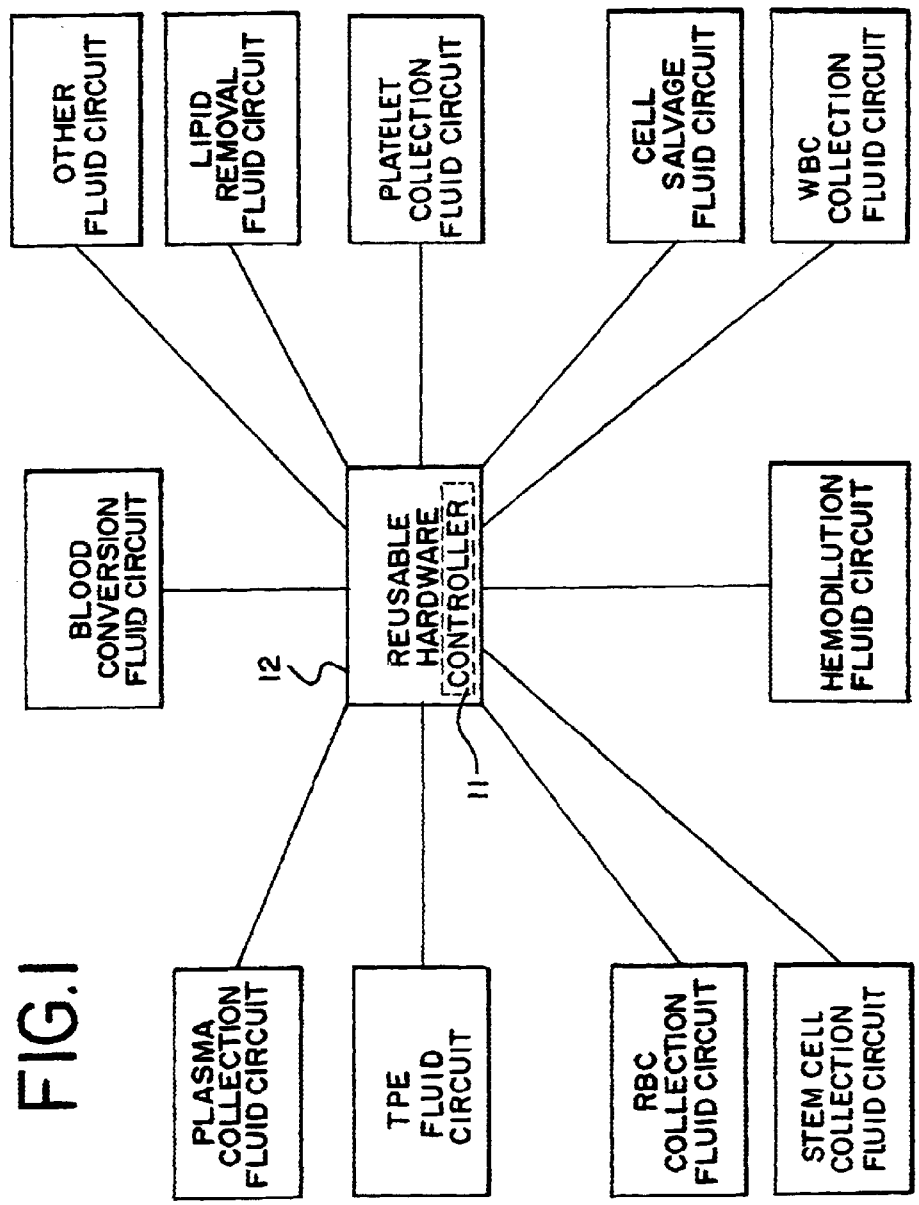
FIG. 1 is a diagram showing the re-usable hardware component or module of the present invention and some of the available disposable fluid circuits for use therewith.

Turning now to the drawings, FIG. 1 diagrammatically shows a multi-purpose blood and fluid processing system 10 embodying the present invention.

As generally shown in FIG. 1, automated system 10 includes a re-usable hardware component or module 12. The re-usable hardware component 12 is particularly versatile and may be used with a variety of disposable fluid circuits. Thus, for example, hardware component 12 can be used with fluid circuits for red blood cell collection, plasma collection, platelet collection, white blood cell (leukocyte) collection, stem cell collection, hemodilution, cell salvage, lipid removal from plasma, conversion of red blood cells, cell washing, red blood cell exchange, leukoreduction, other therapeutic plasma treatments and, as will be seen, combinations of such procedures.

Figure 2:
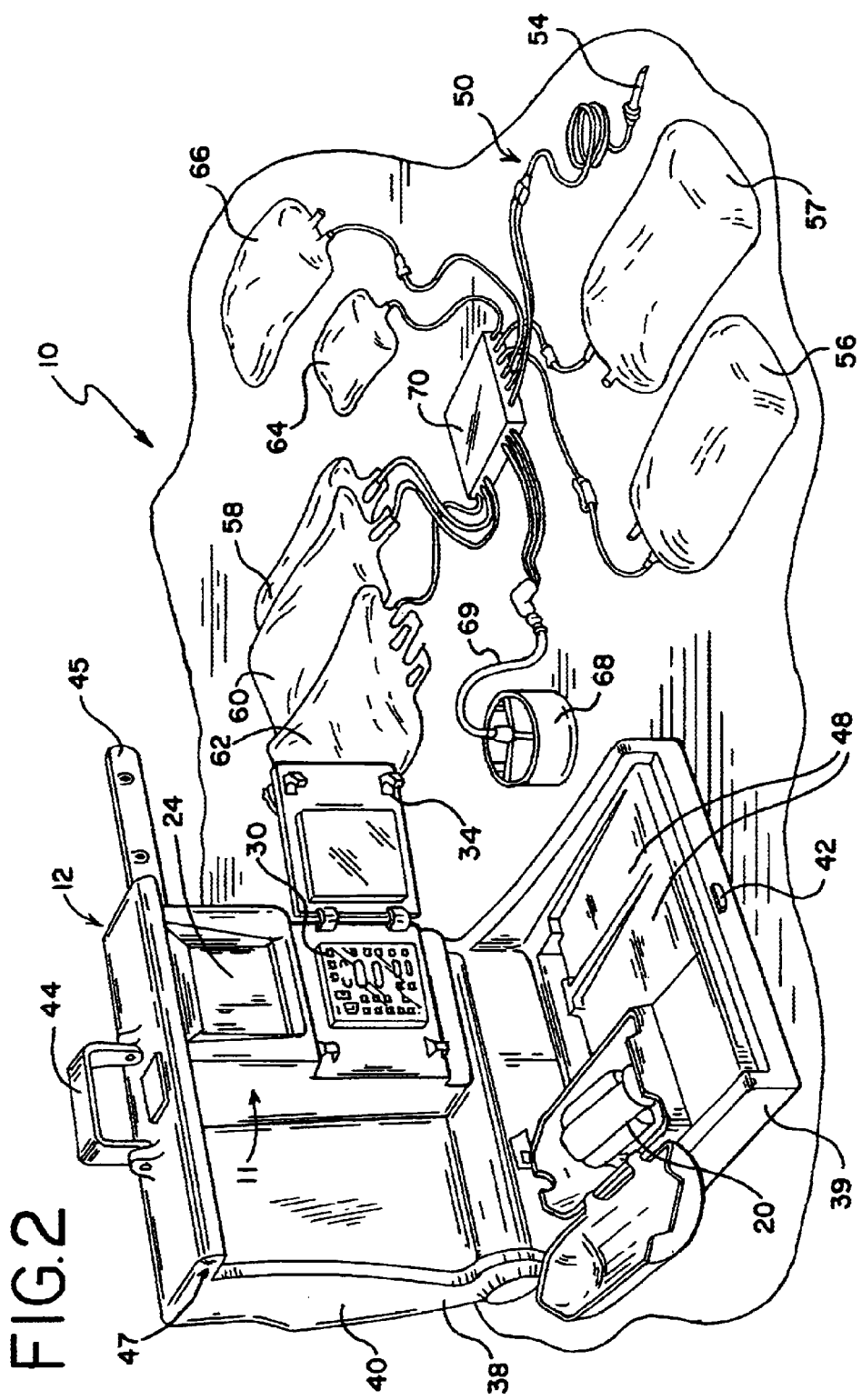
FIG. 2 is a perspective view of a automated system that may be employed with the present invention, including the re-usable component and the disposable fluid circuit.

One embodiment of the automated, multi-purpose blood and fluid processing system that may incorporate the present invention is shown in FIG. 2. As shown in FIG. 2, automated system 10 includes a re-usable module 12 and a disposable fluid circuit 50 for use in association with re-usable component 12.

Fluid circuit 50 includes an array of tubing and interconnected containers typically made of a sterilizable, plastic material. Fluid circuit 50 is intended for a single use (i.e., disposable, not re-usable). As shown in FIG. 2, fluid circuit 50 includes a venipuncture needle 54 for insertion into the vein of the donor or patient. This needle 54 is attached to tubing, which provides a flow path for the blood withdrawn from the donor or patient. Needle 54 can also be used to return selected components to a donor or patient in a so-called "single-needle procedure. Alternatively, circuit 50 may use a "double-needle" configuration, known to those of skill in the art, where separate needles are used for withdrawal and return.

As shown in FIG. 2, fluid circuit 50 includes several containers for temporary and/or longer-term storage of the separated components, and for holding fluids used during the procedure, such as an anticoagulant, saline, and any other treatment or replacement fluids required for the procedure. Containers 56, 57, 58, 60, 62, 64, and 66 are also typically made of a sterilizable, plastic material.

Fluid circuit 50 further includes separation chamber 68. Separation chamber 68 is intended for mounting on the separator of the re-usable device 12. As shown generally in FIG. 2, and in more detail in FIG. 2A, in one embodiment, separation chamber 68 may be pre-formed by injection molding from a rigid, biocompatible plastic material, such as a non-plasticized medical grade acrilonitrite-butadiene-styrene (ABS).

Figure 2A:
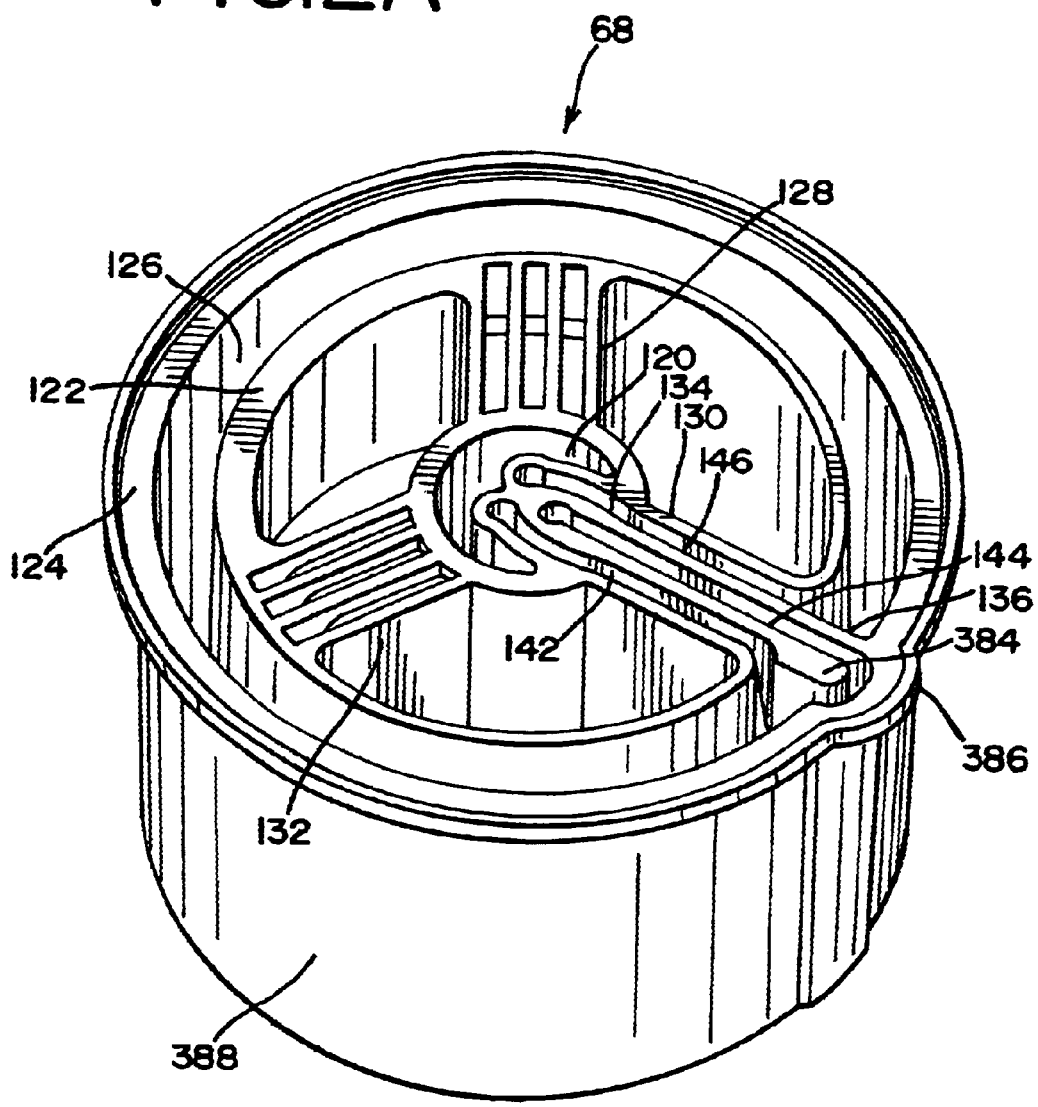
FIG. 2A is an enlarged, perspective view of the separation chamber of the fluid circuit of FIG. 2 which can be employed in the automated system of the present invention.

As further shown in FIG. 2A, separation chamber 68 includes a base 388 with a center hub 120. Hub 120 is surrounded radially by inside and outside annular walls 122 and 134, which define a circumferential blood separation channel 126. Alternatively, chamber 68 may include first and second sub-chambers. The bottom of channel 126 is closed by a molded annular wall. The top of channel 126 is closed by a separately molded flat lid (not shown), which can be secured to the top of chamber 68 by welding or other securing means.

Chamber 68 also includes passageways 142, 144 and 146, which extend from hub 120 and communicate with channel 126. During processing, blood is introduced into passageway 146 at the underside of base 388 via an attached multi-lumened tube or umbilicus 69 (shown as in FIG. 2). Blood enters the channel 126 where it is separated into heavier and lighter components. The heavier components occupy the outer periphery of the channel, while the lighter component occupies the channel interior. The separated components are withdrawn through passageways 142 and 144. Introduction and separation of blood using chamber 68 is described in more detail in U.S. Pat. No. 6,325,775, previously incorporated by reference.

Fluid circuit 50 further includes a cassette 70 which provides a network of flow path segments in fluid communication with and in association with numerous valving and pumping stations. Cassette 70 provides a centralized, programmable, integrated platform for all the pumping and valving functions required for a given blood processing procedure. A more detailed view of cassette 70 is provided in FIGS. 4 and 5. Cassette 70 interacts with the pneumatically actuated pump and valve station 30 on re-usable module 12 described below.

Figure 3:
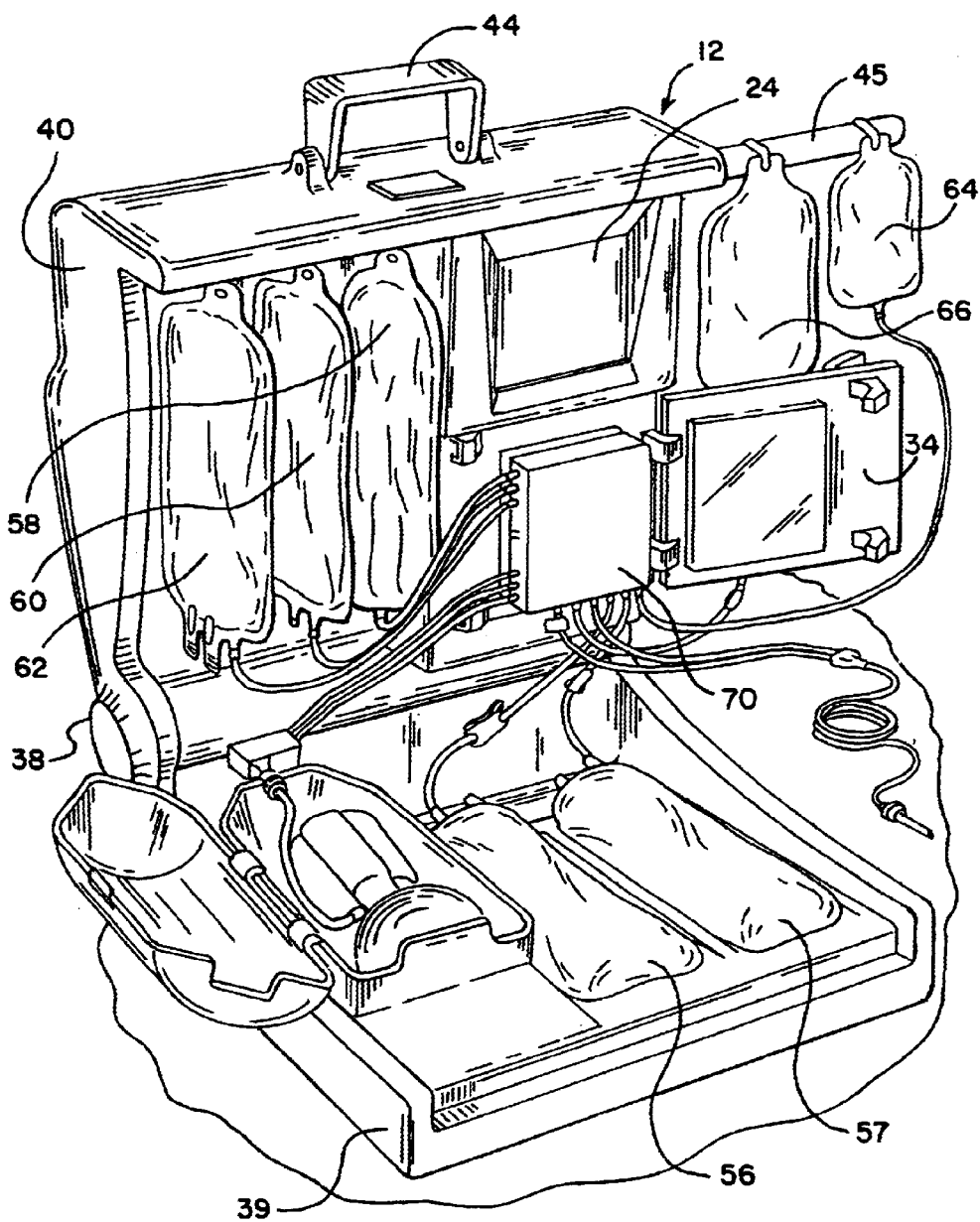
FIG. 3 is a perspective view of an automated system that may be employed with the present invention with a disposable fluid circuit mounted on the re-usable device.
Figure 4:
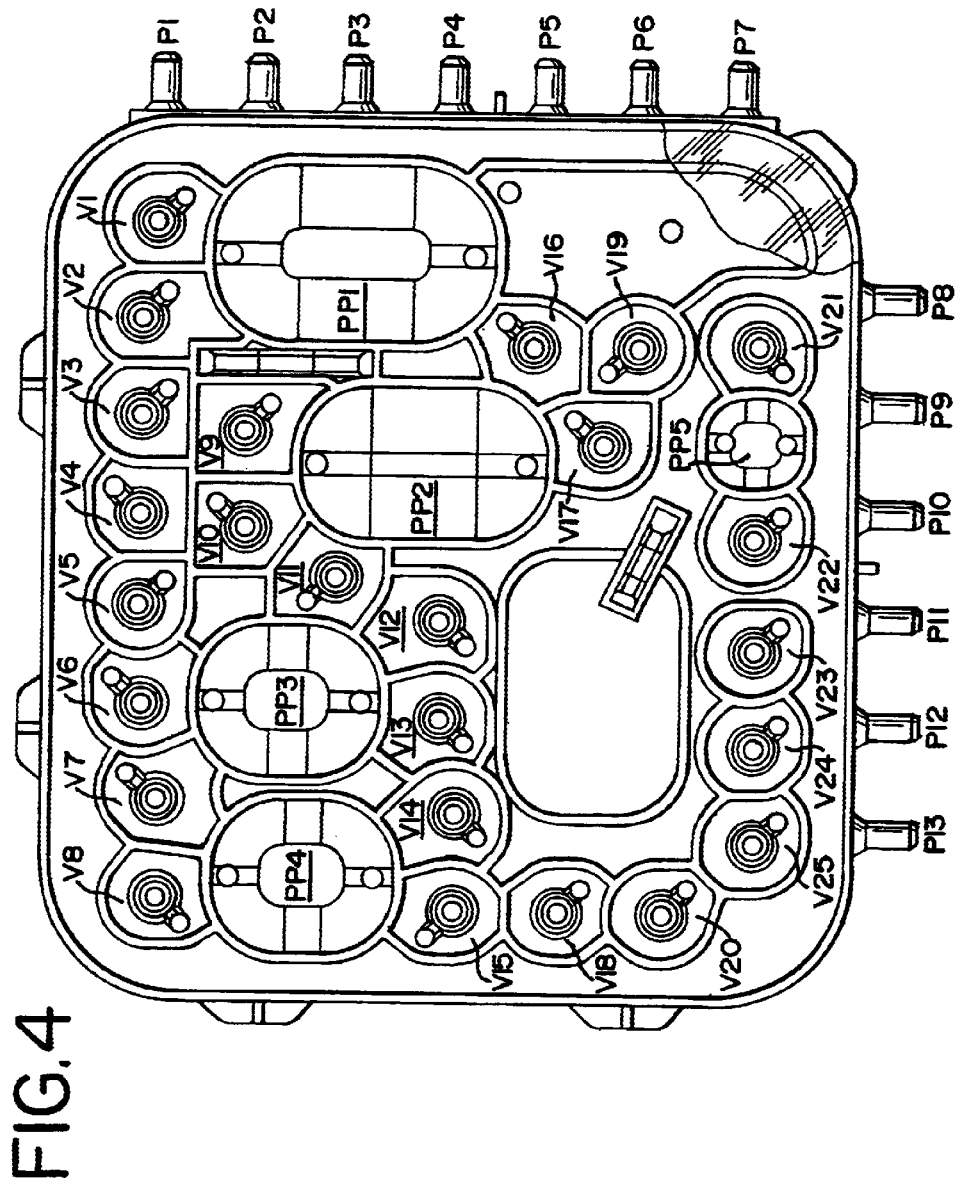
FIG. 4 is a plane view of the front side of a cassette of the fluid circuit of FIG. 2.
Figure 5:
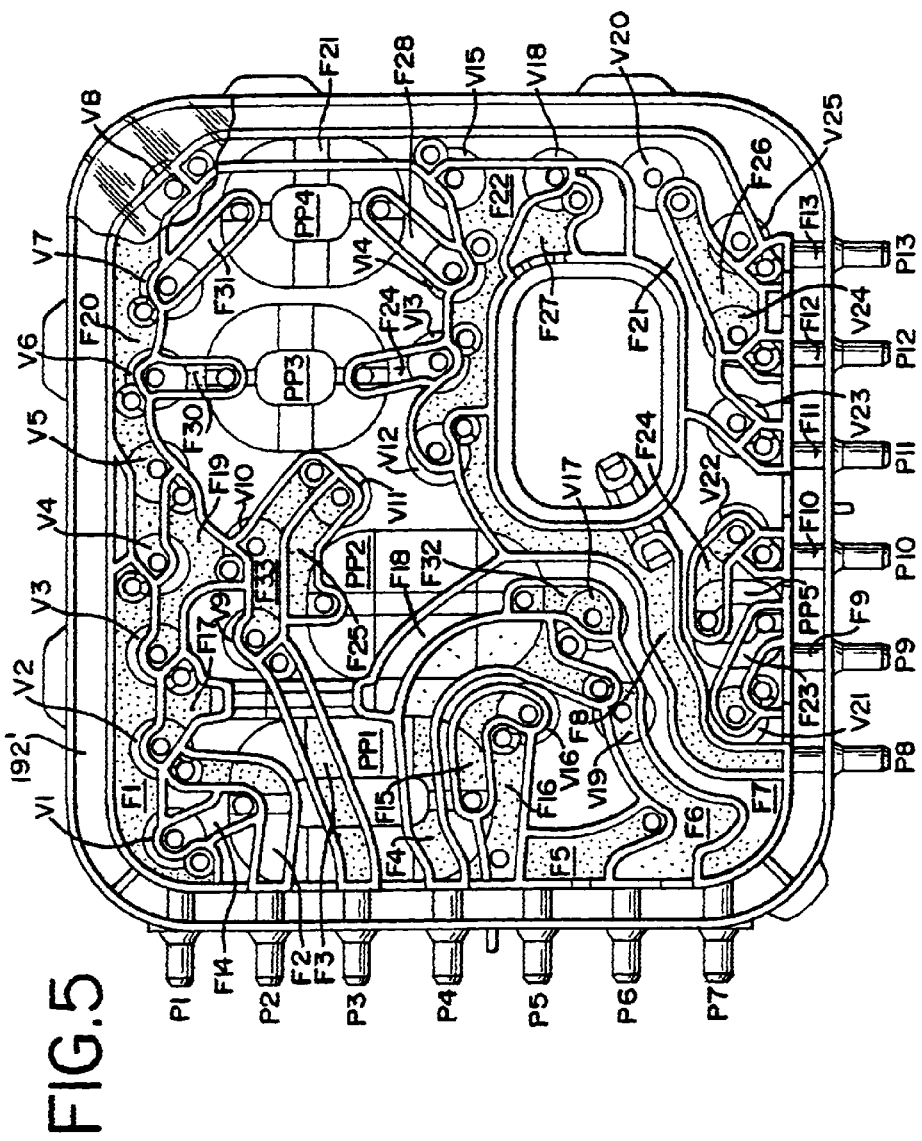
FIG. 5 is a plane view of the back side of the cassette shown in FIG. 4.
Figure 11:
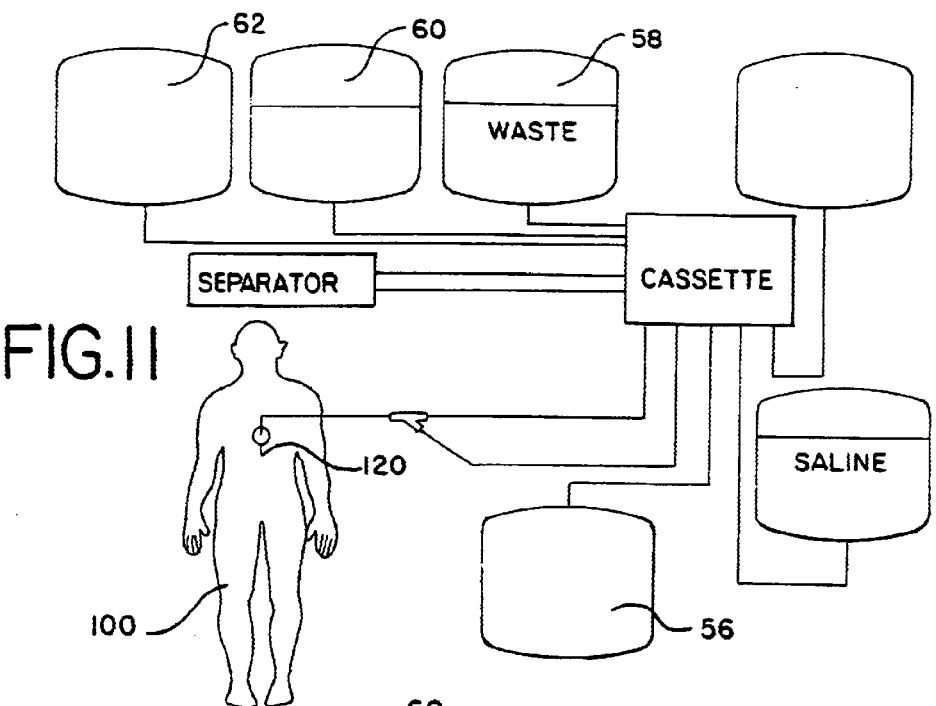
FIG. 11 depicts the fluid circuit for an automated cell salvage system and procedure embodying the present invention cell salvage procedure.

As shown in FIGS. 4 and 5, cassette 70 has an array of interior cavities formed on both the front and back sides. The interior cavities define the valve stations and flow paths. Pump stations PP1 to PP4 are formed as wells that are open on the front side of the cassette 70. The valves V1 to V23 are likewise formed as wells that are open on the front side of cassette 70. The liquid flow paths F1 to F38 are formed as elongated channels that are open on the back side of cassette 70, except for liquid paths at F15, F23, and F24, which are formed as elongated channels that are open on the front side of the cassette 70. The pre-molded ports P1 to P13 extend out along two side edges of the cassette 70. As shown in FIG. 3, the cassette 70 is vertically mounted for use in the pump and valve station 30 described below. In this orientation, ports P8 to P13 face downward, and the ports P1 to P7 are vertically stacked one above the other and face inward.

Cassette 70 is preferably made of a rigid, medical grade plastic material. Flexible diaphragms overlay both of the front side and back side of cassette 70. The diaphragms are preferably made of flexible sheets of medical grade plastic. The diaphragms are sealed about their peripheries to the peripheral edges of the front and back sides of cassette 70. Interior regions of the diaphragms can also be sealed to interior regions of the cassette body.

The action of the pump and valve stations is controlled by a pneumatic pressure source which supplies negative and positive air pressure. As shown generally in FIG. 2 and described in more detailed in U.S. Pat. No. 6,325,775, under the control of the controller 11, a pneumatic pressure source selectively distributes the different pressure and vacuum levels to the pump and valve stations. These levels of pressure and vacuum are systematically applied to the cassette 70 to route blood and processing fluids. The details of the cassette, the pump and valve station 30, and the transport of blood and processing fluids through the cassette are set forth and described in U.S. Pat. No. 6,325,775, previously incorporated by reference.

Turning now to the re-usable hardware component or module, re-usable component 12 includes (at least one) means for effecting separation of blood components or "separator" 20. In one embodiment, separator 20 is cooperatively associated with the chamber 68 of the fluid circuit. In a more particular embodiment, separator 20 is adapted to receive the separation chamber of the fluid circuit (described above) and effects separation of whole blood or a blood fraction into two or more components. In a preferred embodiment, separator 20 may be a rotatable centrifuge. However, it will be understood that separator 20 is not limited to a separator that utilizes a centrifugal separation principle. Accordingly, separator 20 may employ a different separation principle, such as a magnetic drive for receiving a spinning membrane as described, for example, in U.S. Pat. No. 5,194,145. In another embodiment, separator 20 may also be a separation column with its own integral chamber or passageway. Separator 20 may also be a filter. In the preferred embodiment, where separator 20 is a centrifuge, the spinning action of the centrifuge separates the blood components (within separation chamber 68) by density. For example, the spinning action of the centrifuge can separate whole blood into the more dense red cell component and a less dense plasma component.

Re-usable component 12 also houses the internal computer or controller 11. The programmable controller includes pre-programmed instructions for carrying out several different blood and fluid processing procedures, allowing the operator to select from a menu, the particular procedure or procedures desired. The controller also includes pre-programmed instructions which selectively activate pumping of fluid and the opening and closing of valves in the fluid circuit described above. The controller may also include data storage capability for storing donor/patient information, processing or collection information and other data for later downloading or compilation.

As further shown in FIG. 2, re-usable device 12 includes a control panel such as flat screen display 24 for displaying the status of the procedure as well as providing a touch panel screen to allow for operator interface with the system. Data output capability may also include standard parallel or serial ports or other network connection capability, as desired, for communication with other computers or networks.

Device 12 further includes pump and valve station 30. As indicated above, pump and valve station 30 is designed to mate with corresponding structures of cassette 70. Pump and valve station 30 contains four pump actuators PA1 to PA4 and twenty-three valve actuators VA1 to VA23. The pump and valve actuators are oriented to form a mirror image of the pump stations PP1 to PP4 and valve stations V1 to V23 of cassette 70. During operation, pump and valve station 30 (and, more specifically, pump and valve actuators PA(N) and VA(N)), apply positive and negative pressure upon cassette 70 and the corresponding pump and valve stations therein, to direct liquid flow through the flow path segments defined therein. Access to pump and valve station 30 is obtained through door 34.

All of the above-described parts of re-usable device 12, such as separator 20, controller 11, pump and valve station 30, and display screen 24 are mounted inside a portable housing or case 38. Case 38 is suited for set-up and operation upon a table top or other smooth and flat surface. Case 38 includes a base 39 and hinged lid 40 which opens and closes. Lid 40 includes latch 42 for releasably locking the lid. Lid 40 further includes a handle 44, which the operator can grasp for easy transport of case 38 to a collection site, hospital, etc. Case 38 is made by molding and, preferably, of a light-weight, durable plastic material.

For supporting containers in a hanging position, lid 40 includes hooks (not shown) for hanging containers of saline, anticoagulant or other treatment or processing fluid. Similarly, a retractable hanger 45 is provided for supporting one or more collection containers in which whole blood and/or separated blood components are (at least temporarily) stored. Hanger 45 and hooks are preferably mounted on a scale 47 within lid 40 to allow automated measurement of the amount of whole blood or blood component collected.

Inclined container support surface 48 provides additional areas within the case for supporting containers associated with the disposable circuit 50. One or more areas of the support surface 48 may be heated, if desired, to warm the solution of the container prior to infusion to the donor or patient.

As discussed above, controller 11 includes a microprocessor and pre-programmed software. Although some interface and involvement by the operator is required, many of the functions of the automated system 10 are automatically controlled by controller 11.

For example, as shown in FIG. 6 after the operator turns on the power to the re-usable device 12, the system automatically undergoes a system check procedure to confirm that all electrical and mechanical components of the device 12 are functioning properly and within preset parameters. If during the system check the controller detects a problem, the system may generate an audible alarm which prompts the operator to intervene. If the system successfully completes the system check, the system may prompt the operator to select the desired procedure.

As shown in FIG. 6, the automated system allows the operator to select from a variety of procedures. For example, the operator may select a red cell collection (apheresis) procedure, a plasma collection procedure a platelet collection procedure, a white blood cell collection procedure, a stem cell collection procedure.

In addition, the operator may select from a one or more other additional procedures. Thus, the operator can select a first procedure to separate whole blood into two or more components, and also instruct the system to perform another additional treatment or other processing procedure including the separated component(s). Alternatively, the operator may directly select one of the additional procedures, which already combines aspects of the above-mentioned apheresis procedures with additional "downstream" blood processing and/or treatment protocols.

As shown in FIG. 6, these additional procedures include procedures for hemodilution, plasma treatment, such as lipid removal, the conversion of cells, cell salvage and other procedures including, but not limited to, therapeutic plasma treatments, removal of certain compounds from plasma using monoclonal antibodies, magnetic, para-magnetic, and other beads. Additional supplemental procedures involving the separated components of blood may also be performed.

In any event, once the operator has selected the desired procedure, under the control of the controller 11, the system prompts the operator to load the appropriate fluid circuit. Referring back to FIG. 1, it is shown that re-usable device 12 is adapted to receive any one of a variety of disposable fluid circuits. Each of the enumerated procedures may require its own unique disposable fluid circuit or, more preferably, a disposable fluid circuit will be suitable for two or more procedures.

Most of the disposable fluid circuits will have many common elements such as a venipuncture needle, anticoagulant container, saline container, storage containers for red blood cells, plasma or whole blood, a separation chamber and the cassette 70. As mentioned above, each procedure may have its own unique disposable fluid circuit. However, it is also possible that a universal fluid processing circuit can be used and any additional required containers of fluid (e.g., treating agents), additional separators or other components can be easily attached at the time of use. These additional fluid circuit components can be connected to the universal set in a sterile manner in ways that are well known to those of skill in the art. Any additional tubes or flow paths can be attached to existing ports (e.g., P13) on the cassette and the system programmed to perform the additional procedures.

The versatility of the cassette, with its flow path segments that can be interconnected in a variety of ways through selective opening and closing of valves coupled with the programmable microprocessor in the controller lends itself particularly well to the automated system of the present invention. It allows the system to be used with different fluid circuits, to perform a variety of different procedures or protocols, and allows the system to combine aspects of apheresis with additional downstream treatment or processing of blood components.

Once the fluid circuit 50 has been mounted on the re-usable device 12, the system, under the control of the controller 11, will verify that the correct disposable has been loaded and/or that it has been loaded properly. Once proper loading of the disposable processing circuit has been confirmed, the system will automatically initiate a priming sequence based on the selected protocol. Typically, the priming sequence will include priming the fluid circuit with anticoagulant and/or saline. In addition, if a particular treatment or replacement fluid is intended for use in a particular procedure, the system may also prime the disposable fluid circuit with such fluid or the patient's or donor's blood.

The system may allow the operator to enter desired patient or donor data, such as height, weight, gender, hematocrit, or any other donor or patient characteristic that the controller may utilize during the course of the procedure. Entry of donor data may occur before or after prime. For example, the system may use the above-described donor data to determine flow rates, and/or duration of a particular step. After prime and entry of any required donor data, the system prompts the operator to begin the procedure.

FIG. 7 shows an automated system embodying the present invention including a typical fluid circuit. As shown in FIG. 7, whole blood is withdrawn from donor 100 and introduced into cassette 70 via line (tubing) 74. Anticoagulant from container 56 is likewise drawn into cassette 70. Anticoagulant enters through one of the ports (e.g., P10) of cassette 70. Controller opens the selected valve(s) to allow anticoagulant flow through the fluid segment, and establishes flow communication between the anticoagulant line 75 and line 74 to combine anticoagulant with the whole blood being withdrawn from the patient.

Anticoagulated whole blood is introduced into container 58, which serves as an interim whole blood source. As described above, the hardware component 12 can include weight scales. Thus, container 58 is suspended from a weight scale so that when the required amount of whole blood is collected a sensor attached to the weight scale prompts the controller and the draw cycle is terminated. The controller then initiates pumping (by controlling the pump and valve station) of whole blood from container 58 into the separator.

The separator separates whole blood into two or more components. (It will be understood that the separator may be cooperatively associated with separator chamber 68 of the fluid circuit, either physically or as described in, for example, U.S. Pat. No. 5,194,145, incorporated herein by reference.) In one embodiment, separation of whole blood results in a plasma component and a red blood cell component. The separated plasma and red cell components may be withdrawn from separation chamber 68 and collected in separate containers 60 and 62 for temporary storage.

At this point, depending on the procedure or protocol selected (see FIG. 6), further processing of one or both of the separated components may be initiated by the system. Thus, for example, if the additional procedure involves treatment of the separated component, fluid circuit 50 may include a treatment fluid container 64. In another embodiment, if the additional procedure requires administration of a replacement fluid (to, for example, provide the biological function of the withdrawn component), container 64 may include a replacement fluid.

In any event, further processing or treatment of the separated component may take place in separation chamber 68, one of the containers 60 or 62, or, if required, a second and separate separator (shown in dashed lines in FIG. 7 and labeled "Separator 2"). The second separator may utilize the same separation principle as Separator 1. Thus, in one embodiment, both Separators 1 and 2 may be centrifuges. In another embodiment, one of the separators may be a centrifuge while the other separator may be a drive mechanism for cooperation with a rotating member and separation membrane of the type described in U.S. Pat. No. 5,194,145. In another embodiment, one of the separators may be a centrifuge or a drive for a rotating membrane and the other separator can be a filter medium or a separation column.

The blood component separated in Separator 1 can be directly introduced into Separator 2 for further treatment and/or processing. Alternatively, blood component can be introduced into cassette 70 from where it can be directed and/or pumped into Separator 2. Likewise, upon exiting Separator 2, the separated (and/or treated) component can be directly reinfused back to the donor, as shown by dashed line 87, or through cassette 70 and return line 84.

Although FIG. 7 shows a single vein access point (i.e., single needle) for withdrawal of blood and return of blood component, it will be understood that the fluid circuit shown in FIG. 7 (or any one of the other FIGS. 8–12) may also utilize a so-called "double-needle" configuration described above.

Once treatment is complete, the desired component (red blood cells or plasma) can be returned to the donor or patient via line 84. As will be described below, depending on the procedure, there may be variations to the general separation and processing sequence described above.

A more particular example of a system embodying the present invention is shown in FIG. 8. FIG. 8 shows an automated system and procedure for the automated pre-surgical withdrawal of blood, separation into plasma and red blood cells, followed by the return of plasma and infusion of one or more replacement fluids (i.e., "hemodilution").

A system of the type shown in FIG. 8 is particularly useful in the collection of autologous blood from a patient just prior to a surgical procedure. The plasma component is returned and is supplemented with a volume replacement fluid (such as saline) and a blood substitute which can provide the same biological function (i.e., oxygen transport) as the collected red blood cells.

As shown in FIG. 8, whole blood is withdrawn from a patient just prior to the surgical procedure. The whole blood is withdrawn through line 74 and introduced into cassette 70 in the manner generally described above.

Whole blood is combined with anticoagulant and the anticoagulated whole blood may be introduced into container 58 or immediately introduced into the separator. Once inside the separator and, more particularly, the separation chamber 68 associated with the separator, whole blood is separated into a red blood cell component and a plasma component. The red cell component is removed from the separator (by pumping of the pump stations in the cassette 70) and collected in container 60 where it is stored until needed (if needed) during or after surgery. If long-term storage of red cells is required, the collected red cells may be combined with a red blood cell preservative solution such as ADSOL® or Erythro-Sol, available from Baxter Healthcare Corporation of Deerfield Ill. Administration of a preservative (stored, for example, in container 57 (FIG. 2) can also be controlled by controller 11.

The separated plasma can be introduced into container 62 from where it can be metered back to the patient during surgery or, in the alternative, immediately returned to the patient. In another alternative, plasma (with platelets) may be returned to the patient after surgery, at or around the time that the red blood cells are returned.

In order to compensate for the lost volume of red blood cells, a volume replacement fluid such as saline may also be administered to the patient. In addition, because red blood cells include hemoglobin, an oxygen carrying compound in blood, a blood substitute or other synthetic oxygen carrying compound that can perform the same oxygen transport function as the red blood cells may also be administered to the patient. Such blood substitutes and/or oxygen carrying compounds are known and are available from Alliance Pharmaceutical Corporation of San Diego, Calif., and are described in U.S. Pat. No. 5,865,784. Other blood substitutes known to those of skill may also be used.

The blood substitute may be combined with the saline or administered separately either before or after administration of the saline. In addition, other volume replacement fluids in lieu of saline (which is a crystalline solution) may also be used as the volume replacement fluid. This includes colloidal solutions, such as dextran and albumin.

In accordance with a present invention, the system 10 can automatically determine the amount and flow rate of the fluids, i.e., saline and a blood substitute required. In one embodiment, the controller can be pre-programmed to administer the selected amount of saline or other fluid and a replacement fluid having a known biological function, such as a blood substitute, based on the amount of the red blood cells collected as measured by the weight scale 47 in hardware component 12. Alternatively, the system can determine the amount (and flow rate) of the replacement fluid to be administered based on the amount of whole blood withdrawn. In still another alternative, the system can determine the amount of replacement fluid and blood substitute to be administered based on donor data entered at the beginning of the procedure. In any event, the automated system of the present invention provides benefits that manual hemodilution cannot achieve.

For example, by separating whole blood into red cells and plasma, and returning the plasma to the patient, the extracorporeal volume of blood is reduced as compared with the manual systems where whole blood is withdrawn. This results in several benefits not available in "manual" hemodilution.

In the manual hemodilution procedure, the homoglobin concentration of the blood is reduced from approximately 12 mg/dl to 9 mg/dl by withdrawing blood and administering support fluid (3 times the saline or albumin). This represents a total whole blood volume removed of approximately 1L. To replace this lost volume either 1L of albumin or 3L of saline would have to be administered. Three times the volume of saline is necessary due to salinels limited ability to stay within the vascular space. Albumin, being a molecule of larger size, can stay within the vascular space and will not be as quickly excreted as saline.

In accordance with the present invention, because the plasma component is returned to the patient, the volume of fluid removed would be limited to the red blood cell volume which would be approximately 400 ml (based on an average, hematocrit of 40%). When 1L of whole blood is removed with a 40% hematocrit, the total volume of red blood cells removed is 400 ml, with the remaining 600 ml consisting of plasma. To remove an equal amount of red blood cells using the automated system and procedure would require the removal of only 400 ml of concentrated red blood cells with all of the plasma processed by the system being returned to the patient. This reduces the volume removed by 60%. To replace this, only 400 ml of albumin or 1,200 ml of saline would be necessary. This is substantially less than the typical manual hemodilution procedure.

By reducing the volume of saline administered, any potential fluid complication caused by saline can be reduced. Saline can cause fluid overload and tissue edema in patients with renal insufficiency. A large volume saline infusion and associated increase in tissue fluid can necessitate the need for diuretic administration to assist in fluid removal after the surgical procedure.

Another advantage of the automated system of the present invention is that the system can be programmed by the anesthesiologist and the procedure accomplished automatically. The system can add the appropriate amount of anticoagulant to the blood to prevent clotting in the blood storage container and red cell additive solutions can be used as necessary.

Citrate anticoagulation can cause some citrate reactions in patients during apheresis procedures. Citrate reactions are usually controlled by infusion of calcium containing solutions. Using the automated system of the present invention, when the collected blood products are transfused back to the patient, the minimum amount of anticoagulant will be present in the collected blood which, upon transfusion, should cause fewer complications due to citrate transfusion compared to the manual method.

By reducing the volume of fluid removed, the time until blood is to be administered may be prolonged. More importantly, this automated system and procedure can reduce or eliminate the need for non-autologous blood. By eliminating or reducing the need for non-autologous blood, the patient can have limited exposure to non-autologous homologous blood. This can reduce the possibility of post transfusion immunosuppression or inflammatory response due to transfusion of stored blood (cytokine generation during storage).

The automated system of the present invention will allow for the plasma (and platelets) to be returned to the patient. By returning the plasma (and platelets), the patient can more easily maintain normal hemostasis. (In the standard manual hemodilution procedure, severe dilution can cause hemostasis problems which may require infusion of cryoprecipitated clotting proteins (cryoprecipitate) or fresh frozen plasma (FFP). This also occurs during the manual procedure because whole blood is removed which removes platelets and plasma as well as RBC's.)

FIG. 9 shows another application of the automated system of the present invention. In particular, FIG. 9 shows a procedure that results in removal of undesired compounds from blood plasma. More particularly, the fluid circuit and flow system shown in FIG. 9 can be used for removal of lipids from the plasma of the patient.

As shown in FIG. 9, whole blood is withdrawn from a patient 100 via venipuncture and allowed to flow through line 74 into cassette 70, and combined with anticoagulant as previously described. The anticoagulated whole blood may be collected in container 58 until a selected weight is attained. Once the desired amount of whole blood has been collected, under control of the controller 11, the system introduces whole blood into the separator, which can include or is otherwise cooperatively associated with separation chamber 68, where it is separated into red blood cells and plasma. The separated red blood cells may then be returned to the patient immediately, or temporarily stored in container 60 for later return.

The separated plasma may then be further treated to remove lipids (or any other undesirable compounds). In one embodiment, plasma may be combined with a solvent contained in container 64. The solvent is capable of extracting lipids from the plasma. Such solvents are described in, for example, U.S. Pat. Nos. 4,895,558, 5,744,558 and 5,911, 698, which are incorporated herein by reference. Examples of solvents are DIPE (di-isopropylether). of course, other solvents capable of extracting lipids from plasma and known to those of skill in the art may likewise be used.

Plasma and the solvent may be combined in, for example, container 62 or inside separator 68. If combined outside of the separator, the plasma and solvent may then be reintroduced into the separator to further separate plasma from the lipid containing solvent. In a preferred embodiment, the separator is a centrifugal separator of the type shown in FIGS. 2–3 and/or FIGS. 13–16. Centrifugal action results in the separation into a two-phase solution, an upper organic phase that includes the solvent and extracted lipid, and a lower lipid-depleted plasma phase. Under control of the controller, the lipid containing solvent may then be pumped to a separate waste container. The lipid-depleted plasma may be returned to the patient.

Because some of the solvents that may be useful in removing lipids from the plasma may (in certain concentrations) be harmful to the patient, a further processing step that involves purging or otherwise removing any residual solvent from the plasma may be preferred. Thus, after removal of the organic phase, the plasma may be treated with a further washing solution from container 69. Treatment in the washing solution can take place in the separation chamber before return of the plasma to the patient.

Alternatively, as shown in FIG. 9, system 10 may include a second separator (Separator 2) for the cleansing and/or washing step. As set forth above, Separator 2 may employ the same separation principle (e.g., centrifugation) as Separator 1, or more preferably, may employ a different separation principle.

In one embodiment, Separator 2 may be a column packed with coated beads that have an affinity for the solvent. Thus, plasma may be removed from Separator 1 and introduced into column Separator 2 (either directly or via cassette 70) to remove any residual solvent. Plasma that has been passed through Separator 2 may then be suitable for return to the patient. In another alternative, Separator 2 may be filter medium. The system can include an optical detector 83, which is capable of detecting lipids in the plasma being returned. Such detectors are described in U.S. Pat. No. 5,958,250, incorporated herein by reference.

In still another embodiment of the automated system of the present invention, removal of undesired compounds from plasma may be achieved without resort to a solvent-based system. Instead, plasma that has been separated in the separator may be treated or contacted with another material for removing lipids from plasma. For example, in one embodiment, a blood component that has been separated from whole blood can be further treated with particles or beads that have a specific affinity for the compound to be removed. As shown in FIG. 10, container 64 may include the beads or particles. In a preferred embodiment, the beads may be lightweight, simple, hollow (or solid) sphere-like structures. The beads are coated with an affinity material, such as monoclonal antibodies. The beads may have a specific affinity for lipids, sickled cells, immunoglobulins, Factor VIII or other proteins. The beads, preferably, have a density less than the density of plasma. Alternatively, the beads may be of the type described in U.S. Pat. Nos. 5,916,743 and 5,641,622, which are incorporated herein by reference.

In any event, as shown in FIG. 10, whole blood is withdrawn from the donor (or patient) through line 74 and combined with anticoagulant as previously described. Anticoagulated whole blood is collected and temporarily stored in container 58. When a predetermined amount of whole blood has been collected, under the control of the controller, whole blood is introduced in the separator where it is separated into a cellular component and a plasma component. The cellular component can be removed from the separator and collected in, for example, container 60. The plasma component can be combined with beads in container 60 or, to ensure greater contact between the beads and the compound to be removed, in the separator. The controller will cause beads to be pumped into either container 62 or the separator. The bound particle can then be collected in container 62 and the plasma returned to the donor. Alternatively, in another embodiment, plasma may be passed through a filter or other type of medium that has attached to its surface monoclonal antibodies that have a specific affinity for lipids. The filter medium may be a flat sheet or a packed column of the type described above. In addition, the separation medium (e.g., separator 80) may be used to extract or remove lipids or other compounds (through affinity separation) such as IgG, IgM, Factor VIII, and the like from plasma.

Another application for the automated system of the present invention is in the treatment of blood cells, such as red cells, white cells or platelets. In one specific embodiment, the automated system can be used to treat red blood cells with an enzyme to convert, for example, Type-A, Type-B, or Type-AB red blood cells to Type-O red blood cells. Accordingly, as shown in FIG. 10, whole blood is withdrawn from a patient 100, anticoagulated in the manner described above, and separated in separator 68 to provide a red blood cell component and a plasma component. The plasma component can be collected in container 60 or can be returned to the donor immediately. The red blood cell component can be temporarily collected in container 60. Under the control of controller 11, the red blood cell component can be combined with a solution (stored in container 64) that includes a particular enzyme suitable for the red blood cell conversion. Examples of such enzymes are included in U.S. Pat. Nos. 6,175,420 and 5,671,135, which are incorporated by reference herein. The treated red blood component may then be collected and stored in container 62. In addition, if Type-O blood cells are to be stored long term (e.g., up to 42 days), a preservative solution of the type described above can be added to the red blood cells. In another treatment-type application, red blood cells, platelets or even plasma may be treated to eradicate or inactivate pathogens present in these components.

Another application of the automated system of the present invention can be the salvage of blood during a surgical procedure. As shown, for example, in FIG. 11, whole blood can be collected from the body cavity of a patient 100 undergoing surgery. In this embodiment, fluid circuit will include a suction device 120 instead of a venipuncture needle. Suction device 120 maybe of the type shown in, for example, U.S. Pat. No. 5,976,388, which is incorporated herein by reference. Blood that is removed by suction device 120 is introduced into the separator where it is separated into a red blood cell component and supernatant. The red cell product may then the returned to patient.

Figure 12:
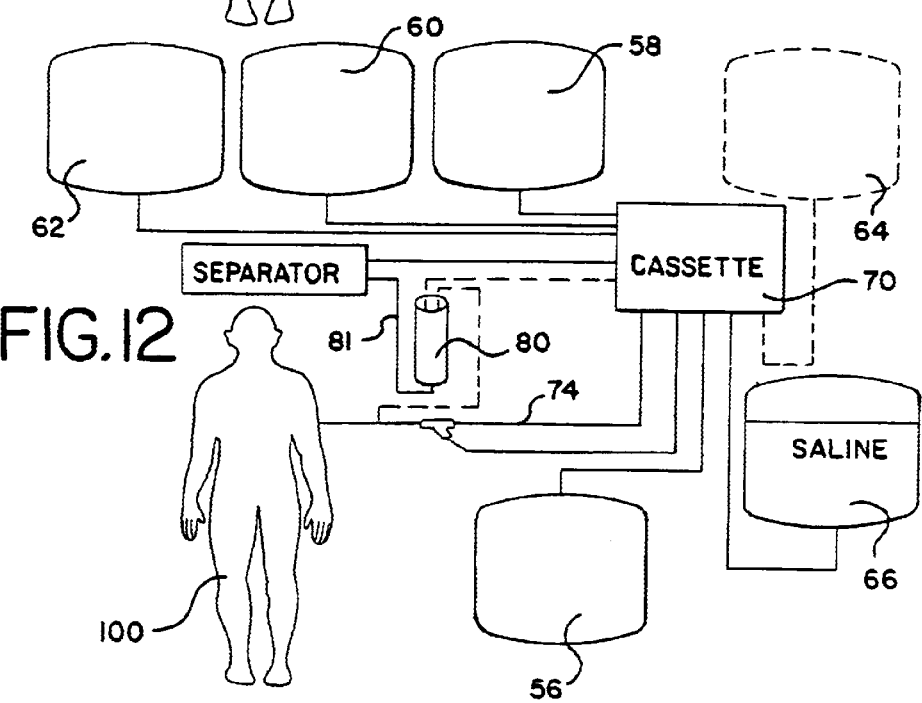
FIG. 12 depicts the fluid circuit for an alternative automated plasma treatment system and procedure embodying the present invention.
Figure 12A:
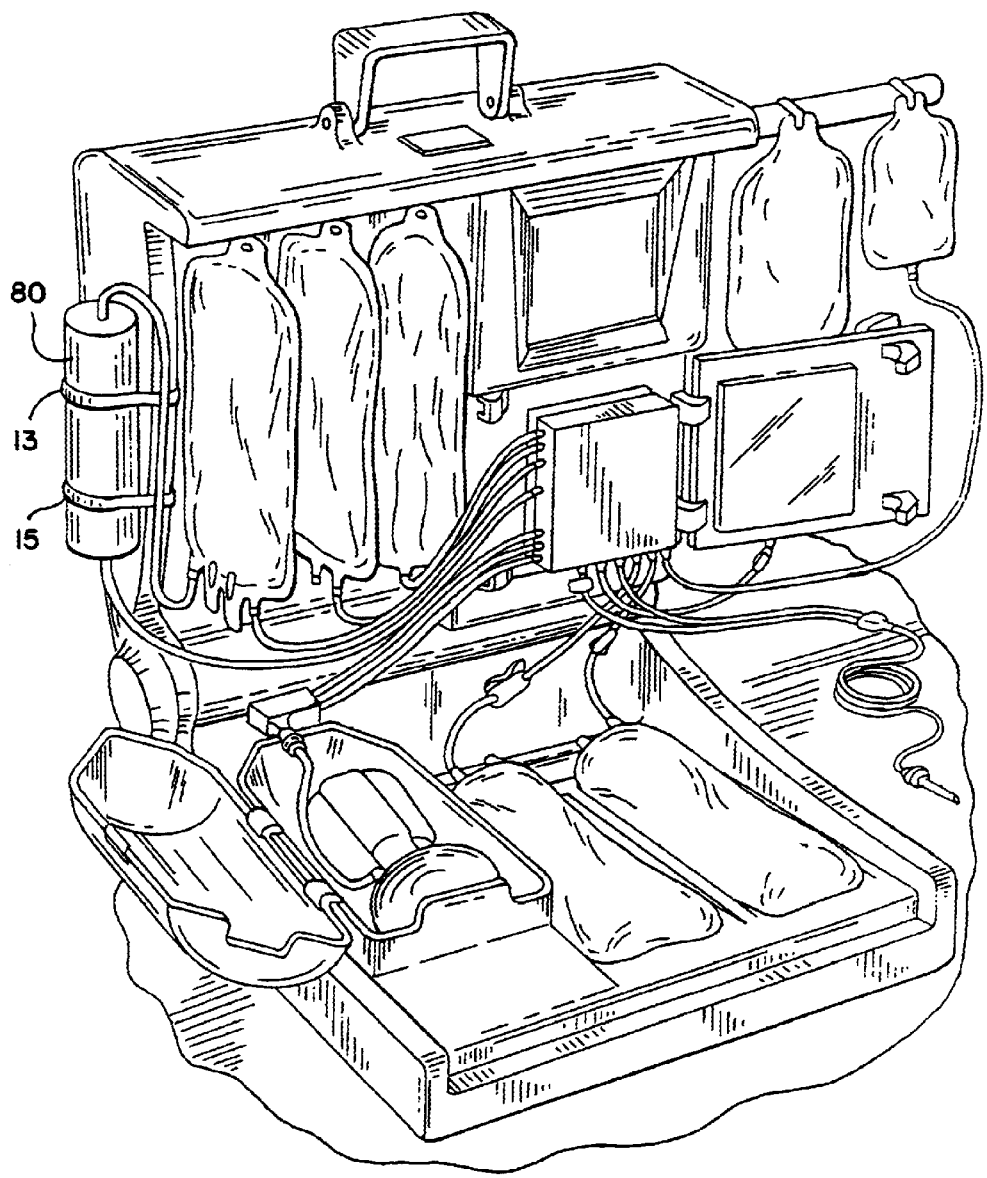
FIG. 12A is a perspective view of an automated system that may be employed with the present invention with a disposable fluid circuit including a separation column mounted on the re-usable component.

Turning briefly to FIG. 12, an alternative, automated system for treating separated plasma is shown. The system includes a first separator and a second separator. As shown in FIG. 12A, the second separator is a separation column 80 that can be used to remove the above-described compounds from plasma. Columns that can be used for such separation are generally disclosed in U.S. Pat. Nos. 5,733,254 and 5,782,792, which are incorporated herein by reference.

As shown in FIG. 12, separation of plasma from whole blood proceeds as generally described above, i.e., in the separator. The separated plasma may be introduced into column 80. It should be noted that plasma can be directly introduced into column 80 via line 81, or can be conveyed by the pumps and valves of cassette 70 (under the direction of the controller) to column 80. Likewise, plasma that has passed through column 80 can be returned via cassette 70, can be directly introduced into line 74 for direct return to the donor, or can be introduced into container 62 from where it is pumped (through cassette 70) back to the donor. Red cells in container 60 may be returned to the donor during processing of plasma.

Column 80 may be provided as part of the fluid circuit 50. In one embodiment, re-usable component 12 can be equipped with clips 13 and 15 for holding column 80, as generally shown in FIG. 12A.

FIGS. 13–16 show an alternative embodiment of another reusable hardware device and fluid circuit that can be used in the automated system and procedure of the present invention. The embodiment shown in FIGS. 13–16 include a centrifuge assembly 200 and a fluid processing circuit 50 for use in association with the centrifuge assembly. The centrifuge assembly includes a reusable hardware device capable of long-term use. The disposable fluid circuits, like the fluid circuits described above, are intended to be a single-use, disposable item.

Like the disposable fluid circuits described above, the fluid circuits shown in FIGS. 13–16 include a processing chamber, shown in FIG. 16, that can be loaded onto a separator of the re-usable device, to centrifugally separate blood components. The separator may separate whole blood into a red blood cell component, a plasma component, a white blood cell component, stem cells or a platelet component. The disposable fluid circuit also includes an array of flexible tubing to convey liquid to and from the processing chamber, described in more detail below.

Fluid circuit 50 includes one or more cassettes 222A, B and C, generally of the type described above. The cassettes shown in FIGS. 14–15 include inter-connectable flow segments and valving stations. In contrast to cassettes 70 described above in connection with other embodiments, the cassettes of this embodiment do not include internal pumping stations. Instead, the cassettes of this embodiment include external tubing loops 223 which engage peristaltic pump rotors 250, which effect movement of fluid through the tubing and the fluid circuit. The details of this embodiment of the automated system are described in U.S. Pat. No. 5,868,696, which is incorporated herein by reference.

Figure 16:
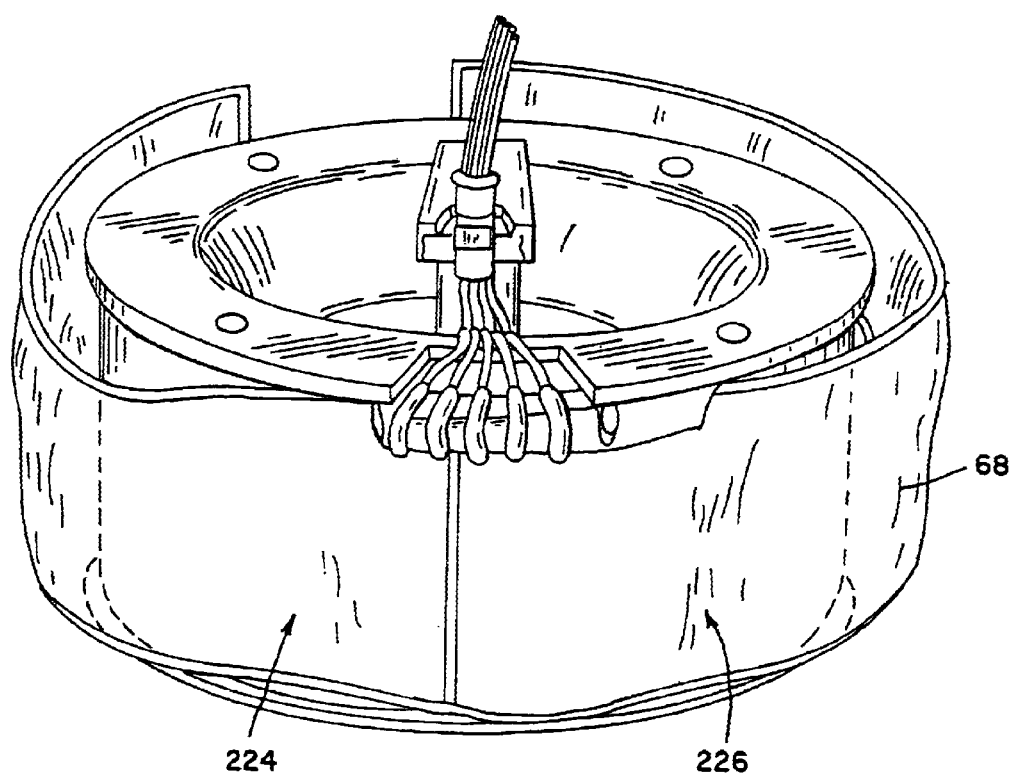
FIG. 16 is an enlarged perspective view of a separation chamber of the fluid circuit of FIG. 14.

As shown in FIG. 16, in the embodiment of FIGS. 13–16, fluid circuit 50 includes a "two-staged" separation chamber 68. Thus, the first sub-chamber 226 can be used to perform a first separation step and the second sub-chamber 224 can be used to perform a second separation step. For example, where a blood component such as plasma or red blood cell is to be treated with a treating agent or described above, plasma can be separated from red cells in the first "sub-chamber" 226 and the treatment carried out in the second "sub-chamber" 224. A treating agent can be directly introduced into the second subchamber or can be combined with the component elsewhere, such as in one of the containers.

The second subchamber can also be used to remove undesirable solvents, compounds, treating agents from the separated component. In most other respects, the blood and fluid processing procedures described above are applicable to the automated system described and shown in FIGS. 13–16. Of course, the chamber 68 may have only a single chamber.

Figure 14:
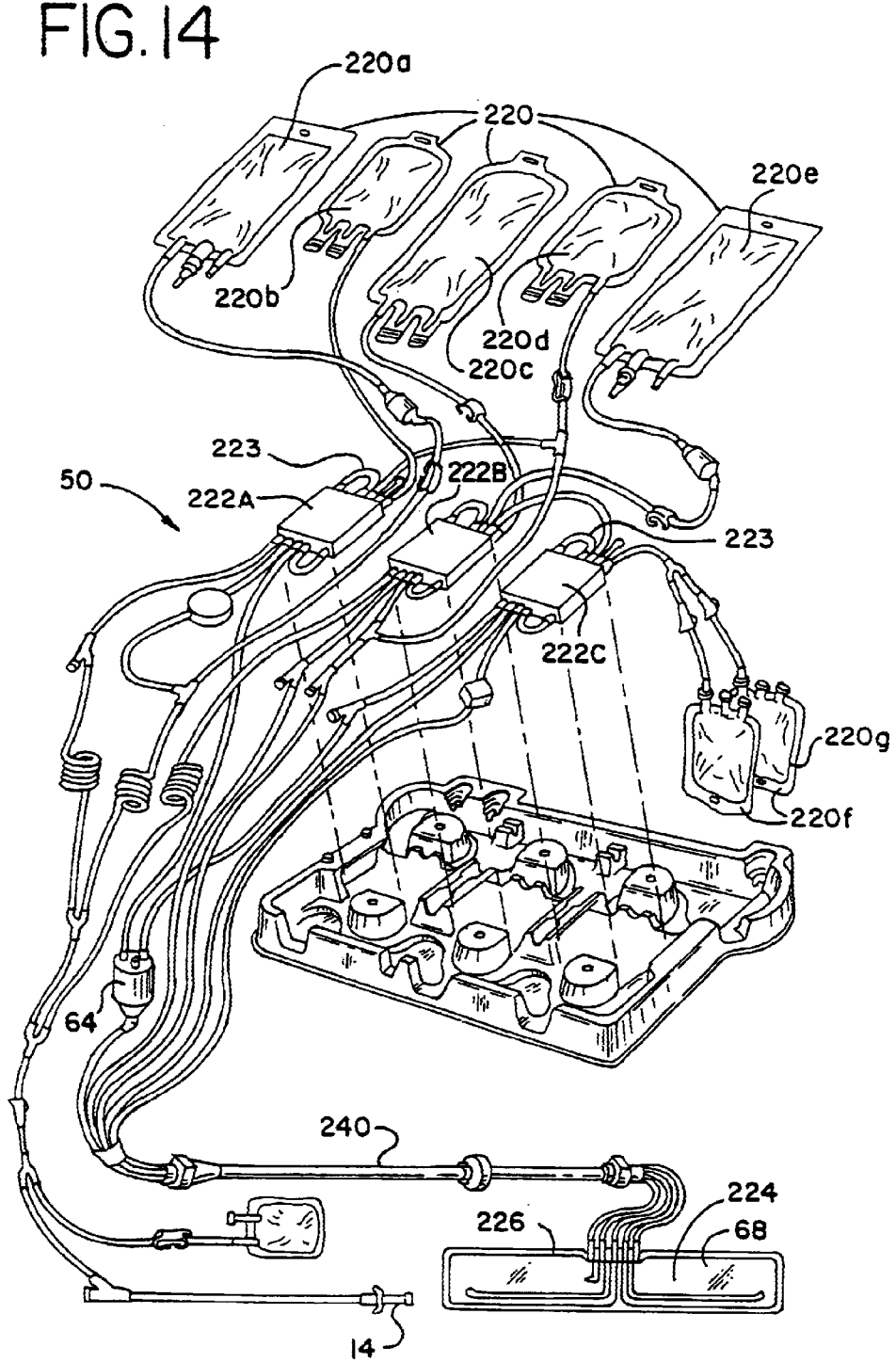
FIG. 14 is a perspective view of a fluid circuit for use with the re-usable device of FIG. 13.
Figure 15:
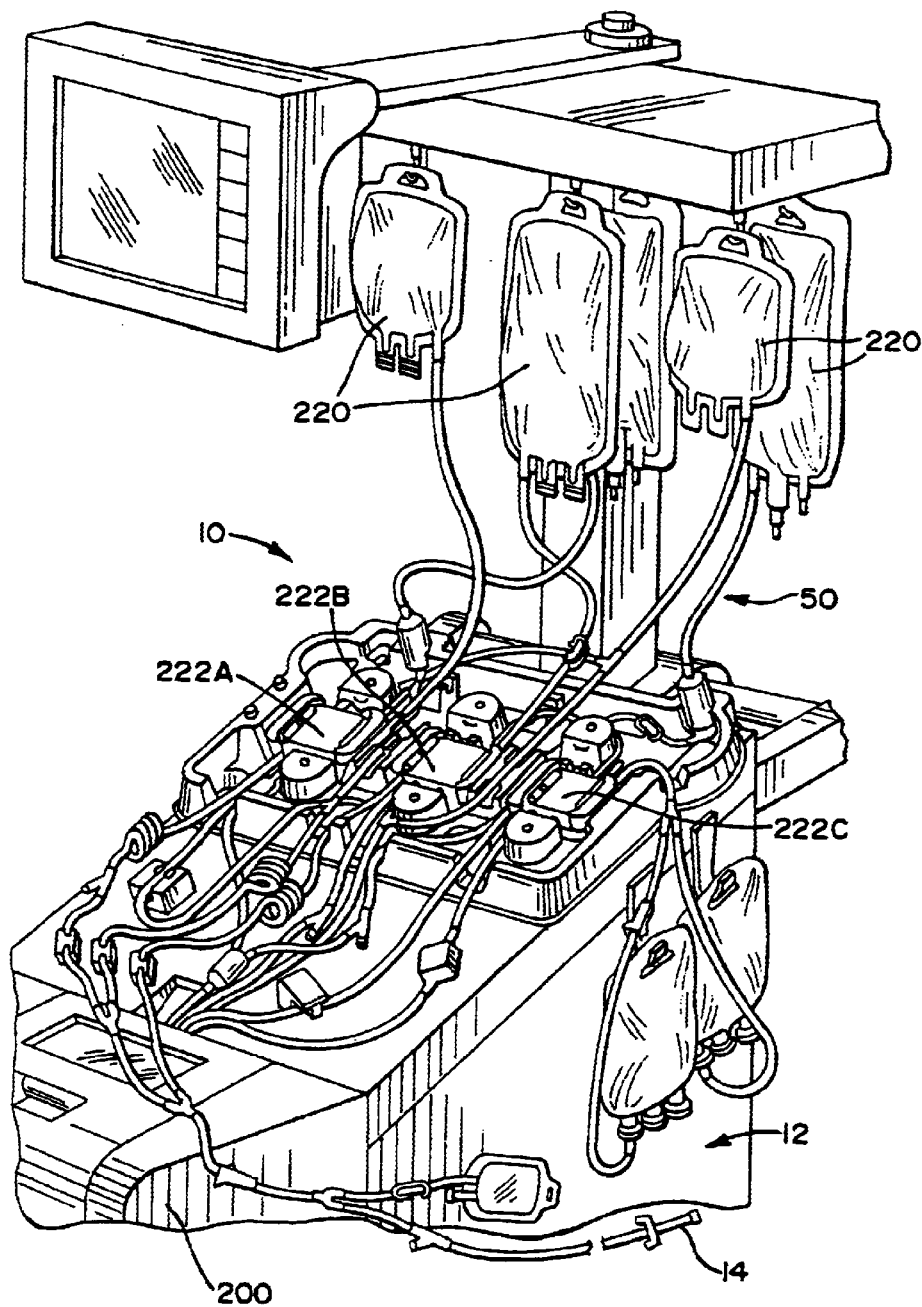
FIG. 15 is a perspective view of the fluid circuit shown in FIG. 14 mounted on the re-usable component.

More particularly, disposable circuit 50 shown in FIG. 14 is adapted for single needle platelet collection. Circuit 50 includes processing chamber 68 having separation and collection chambers 34 and 36. The ports of processing chamber 68 communicate with multi-lumen umbilicus 240 which, in turn, communicates with donor needle 14 and containers 220a–g, either directly or through cassettes 222a–c.

In a typical apheresis procedure, processing circuit 50 is initially primed with saline withdrawn from container 220a. During the draw cycle, the donor's blood is mixed with anticoagulant from container 220e. A portion stored in reservoir container 220b and the remainder is conveyed through umbilicus 240 to separation chamber 68 where it is separated into red cells and platelet rich plasma. The red blood cells are conveyed through umbilicus 240 to red cell storage container 220d. The platelet rich plasma is conveyed through umbilicus 240 to cassette 222c and then back through umbilicus 240 to collection chamber 68 where the platelets are sedimented onto the hi-g wall for subsequent processing. The platelet poor plasma is conveyed through umbilicus 240 to plasma reservoir container 220c. During the return cycle, plasma from container 220c and red cells from container 220d are returned to the donor, while blood held in reserve in container 220b is being processed. After the donation is completed, processing chamber 68 is removed from the centrifuge, the platelets are resuspended and conveyed to platelet storage containers 220f and 220g along with sufficient plasma to provide adequate storage for up to five days.

In accordance with the present invention, many different and additional procedures can be performed with the system shown in FIGS. 13–16, by reconfiguring the interconnections of disposable circuit 50 and providing different containers 220a–g and processing chamber 68. One such reconfiguration provides for the collection of mono-nuclear cells and is described in U.S. Pat. No. 5,980,760, which is incorporated herein by reference. The flexibility to reconfigure the functions and characteristics of disposable circuit 50 is provided, in large part, by the versatility of cassettes 222a–c. Several such different procedures are described below.

For example, when the system of FIGS. 13–16 is used for hemodilution, some red cells are stored for subsequent transfusion, a replacement solution is provided and a supplemental oxygen carrier may be also supplied. As in the mono-nuclear cell procedure of U.S. Pat. No. 5,980,760, only a single separation chamber is required. Thus, the system can be supplied with a single chamber, or the dual chambered embodiment may be used, but only utilizing sub-chamber 226.

The circuit is again primed with saline withdrawn from container 220a. During the draw cycle, blood is again mixed with anticoagulant from container 220e with a portion stored in container 220b and the remainder supplied to separation chamber 68. Separated, packed red blood cells are again stored in container 220d with separated plasma stored in container 220c. During return, sequestered blood from container 220b is conveyed to separation chamber 68, the separated red blood cells collected, while instantaneously separated plasma, along with that plasma previously sequestered in container 220c are returned to the patient along with replacement solution from saline container 220a. Supplemental oxygen carrier held in containers 220f and 220g can also be administered to the patient during the return cycle in a predetermined quantity based upon the amount of red cells collected. An additional tubing section can be provided between saline container 220a and an unused port on cassette 222*a* to facilitate metered control of saline administration during the return cycle.

During the cell salvaging procedure, a patient's extravascular ("shed") blood is withdrawn from the surgical field, washed, and returned to the patient. Disposable circuit 50 can again be reconfigured to accomplish cell salvaging. A reconfigured circuit 50 would again be primed with saline from container 220*a*. Needle 14 would be replaced by a suction wand, not shown and of known construction, and the extra-vascular or shed blood mixed with anticoagulant from container 220*e* and stored in blood reservoir 220*b* until a sufficient quantity is obtained. Upon processing, the stored blood is mixed with saline from container 220*a*, conveyed to separation chamber 68 and separated into now washed, packed red blood cells and a supernatant fluid containing blood plasma and washing solution saline. The packed red blood cells are stored in container 220*d* until required, while the supernatant fluid is collected in waste container 220*c*.

An administration set can be provided to return the packed cells stored in container 220*d* to the patient by known gravity means or a separate return line (not shown) could be provided so that the washed red blood cells could be pumped directly to the patient. Alternatively, extra-vascular or shed blood could be drawn into a stand-alone vacuum cannister (not shown, but of known construction) and withdrawn through needle 14 when processing is desired. As with the hemodilution application above, an addition tubing segment can be supplied between saline container 220*a* and cassette 222*a* to provide metered control of saline during the washing process.

During lipid removal, lipid are removed from a patient's blood. Circuit 50 can again be reconfigured to effect such a removal. The circuit can again be primed with saline from container 220*a*. During the draw cycle, blood is again mixed with anticoagulant from container 220*e* with a portion stored in container 220*b* and the remainder supplied to separation chamber 68. Separated, packed red blood cells are again stored in container 220*d*. The separated plasma is mixed with a solvent held in containers 220*f* and 220*g* and conveyed to secondary separation stage 224 where lipid reduced plasma is produced and conveyed to plasma container 220*c*. The solvent agglutinated lipids can be sequestered in secondary separation chamber 221, or, alternatively, an additional lumen can be provided in umbilicus 240 so that the lipids could be continuously pumped into a waste container connected into an unused port in cassette 222*c* (not shown). Alternatively, affinity based materials could be used in place of solvents to affect removal of lipids, as described above.

As previously discussed, red blood cells having Type-A, Type-B, or Type-AB antigens can be converted to Type-O red cells by certain enzymatic treatments. Disposable circuit 50 can again be reconfigured to affect such a treatment. The circuit can again be primed with saline withdrawn from container 220*a*, or, if desired, primed with blood. During the draw cycle, blood is again mixed with anticoagulant from container 220*e* with a portion stored in container 220*b* and the remainder supplied to separation chamber 68. Separated, packed red blood cells are again stored in container 220*d* and the separated plasma stored in container 220*c*. The plasma is returned during the return cycle. The red cells then undergo enzymatic conversion in a post processing step. The packed red cells are transferred from container 220*d* to container 220*b* and mixed with enzymes from containers 220*f* and 220*g*. The treated red cells are then admixed with saline from container 220*a* and conveyed to separation chamber 68. The washed and treated red cells are again stored in container 220*d*, while the separated supernatant is conveyed to the now unused plasma container 220*c* for subsequent disposal. The process of transferring the red cells from container 220*d* to container 220*b*, admixing the saline from container 220*a* and separated into washed, packed cells and supernatant solution in separation chamber 68 can be repeated as many times as desired.

Alternatively, a normal platelet collection procedure could be performed using disposable circuit 50 with the collected platelets stored in containers 220*f* and 220*g*, as described above. A concurrent red cell product can be collected and stored in container 220*d*. A new container holding the enzymes would be provided and connected into the unused port on cassette 222*c*, so that the collected red cells could be converted to Type-O, as discussed above. As with the hemodilution application above, an additional tubing segment can be supplied between saline container 220*a* and cassette 222*a* to provide metered control of saline during the washing process.

Figure 13:
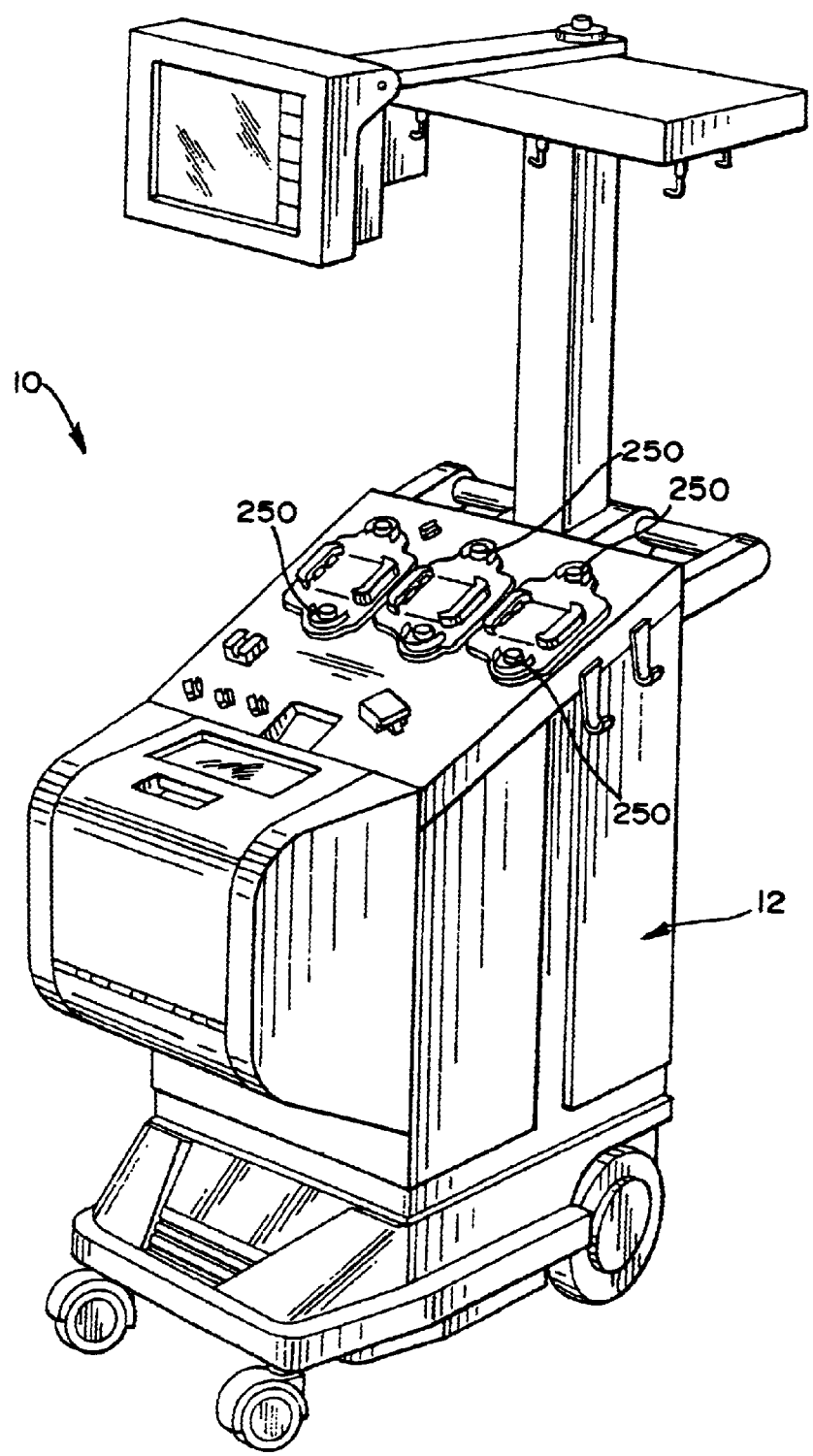
FIG. 13 is a perspective view of the re-usable component of an alternative automated system that may be employed with the present invention.

The many procedures discussed above have been based upon the single needle disposable circuit 50 of FIG. 13, but it should be appreciated by those skilled in the art that a two-needle circuit can also be modified to accomplish the desired procedures as well.

The various features of the present invention are set forth in the attached claims.

That which is claimed:

1. An automated system for withdrawing a selected compound from the blood of a patient comprising:
   (a) a sterile, pre-assembled, disposable fluid circuit comprising:
      (i) means for withdrawing blood from a patient,
      (ii) a separation chamber in flow communication with said withdrawing means, said separation chamber including a first sub-chamber for separating a blood component from blood,
      (iii) a container containing a solvent adapted for extracting a selected compound from said blood component to provide a compound-depleted blood component,
      (iv) means for combining said solvent with said blood component,
      (v) said separation chamber having a second sub-chamber for separating the combination of said blood component and said solvent into a first phase which substantially comprises said compound-depleted blood component and a second phase which substantially comprises said solvent and said compound,
      (vi) solvent removal means for removing solvent from said compound depleted component,
      (vii) a flow control cassette having pre-formed flow path segments therein separated by valve stations for controlling communication between said flow path segments and inlet and outlet ports for communicating fluid through said fluid circuit, and
      (viii) means for returning said compound-depleted blood component to said patient;
   (b) a re-usable module adapted to cooperatively receive said fluid circuit, said re-usable module including:
      means cooperatively associated with said separation chamber for effecting separation of said blood component from the remainder of said blood; and
      means for cooperating with said valve stations to control the flow of fluid through said pre-formed flow paths of said cassette.

2. The system of claim 1 wherein said blood comprises blood plasma.

3. The system of claim 1 wherein said means for effecting separation comprises a rotatable centrifuge.

4. The system of claim 1 wherein said flow control cassette further comprises pump stations for pumping fluid through said flow path segments.

5. An automated system for withdrawing a selected compound from the blood of a patient comprising:
(a) a sterile, pre-assembled, disposable fluid circuit comprising:
   (i) means for withdrawing blood from a patient,
   (ii) a first separation means based on a first separation principle for separating a blood component including said compound from blood, wherein said first means is in flow communication with said withdrawing means,
   (iii) a container containing a solvent adapted for extracting a said compound from said blood component to provide a compound-depleted blood component,
   (iv) means for combining said solvent with said blood component,
   (v) a second separation means based on a second separation principle for separating the combination of said blood component and said solvent into a first phase which substantially comprises said compound-depleted blood component and a second phase which substantially comprises said solvent and said compound,
   (vi) solvent removal means for removing solvent from said compound depleted component,
   (vii) a flow control cassette for controlling flow through said fluid circuit, said cassette having pre formed flow path segments therein separated by valve stations for controlling communication between said flow path segments and inlet and outlet ports for communicating fluids through said fluid circuit, and
   (viii) means for returning said compound-depleted blood component to said patient;
(b) a reusable module adapted to cooperatively receive said fluid circuit, said reusable module including:
   means for cooperating with said valve stations to control the flow of fluid through said pre-formed flow paths of said cassette.

6. The system of claim 5 wherein said re-usable module further comprises a centrifugal separator.

7. The system of claim 6 wherein said first separation means comprises a membrane and said second separation means comprises a chamber for use in association with said centrifugal separator.

8. The system of claim 6 wherein said first separation means comprises a chamber for use in association with said centrifugal separator.

9. The automated system of claim 1 wherein said container includes a solvent for extracting lipids from blood plasma.

10. The automated system of claim 9 wherein said solvent comprises di-isopropylether.

11. The automated system of claim 1 wherein said solvent removal means comprises a wash solution.

12. The automated system of claim 11 wherein said wash solution is within a container in flow communication with said separation chamber.

13. The automated system of claim 1 wherein said solvent removal means comprises a second separator.

14. The automated system of claim 13 wherein said second separator employs a separation principle different from the separation principle employed for separating said blood component from blood.

15. The automated system of claim 13 wherein said separation principle employed for separating said blood component from blood is centrifugation and said second separator employs centrifugation.

16. The automated system of claim 13 wherein said second separator comprises a column packed with coated beads that have an affinity for said solvent.

17. The automated system of claim 13 wherein said second separation comprises a filter.

18. The automated system of claim 5 wherein said container includes a solvent for extracting lipids from blood plasma.

19. The automated system of claim 5 wherein said solvent comprises di-isopropylether.

20. The automated system of claim 5 wherein said solvent removal means comprises a wash solution.

21. The automated system of claim 20 wherein said wash solution is within a container in flow communication with said second separation means.

* * * * *